(12) United States Patent
Jacques et al.

(10) Patent No.: US 12,180,137 B1
(45) Date of Patent: Dec. 31, 2024

(54) SOLID FORMS OF ENANTIOPURE DEUTERIUM-ENRICHED BUPROPION AND METHODS OF USE THEREOF

(71) Applicant: DeuteRx, LLC, Andover, MA (US)

(72) Inventors: Vincent Jacques, Somerville, MA (US); William Perrault, Andover, MA (US)

(73) Assignee: DeuteRx, LLC, Andover, MA (US)

(*) Notice: Subject to any disclaimer, the term of this patent is extended or adjusted under 35 U.S.C. 154(b) by 0 days.

(21) Appl. No.: 18/652,164

(22) Filed: May 1, 2024

(51) Int. Cl.
    C07C 225/06    (2006.01)
    A61K 31/137    (2006.01)

(52) U.S. Cl.
    CPC .......... *C07C 225/06* (2013.01); *A61K 31/137* (2013.01); *C07B 2200/05* (2013.01); *C07B 2200/07* (2013.01); *C07B 2200/13* (2013.01)

(58) Field of Classification Search
    None
    See application file for complete search history.

(56) References Cited

U.S. PATENT DOCUMENTS

| | | | |
|---|---|---|---|
| 3,819,706 A | 6/1974 | Nariman | |
| 8,524,780 B2 * | 9/2013 | Czarnik | C07C 225/16 564/345 |
| 8,735,454 B2 * | 5/2014 | Czarnik | A61P 25/34 564/345 |
| 9,732,031 B2 | 8/2017 | DeWitt et al. | |
| 2009/0076161 A1 * | 3/2009 | Czarnik | A61P 25/34 564/345 |
| 2010/0075950 A1 | 3/2010 | Gant et al. | |
| 2014/0018436 A1 | 1/2014 | Czarnik | |
| 2017/0369420 A1 | 12/2017 | DeWitt et al. | |
| 2021/0387940 A1 | 12/2021 | DeWitt et al. | |
| 2022/0213023 A1 | 7/2022 | DeWitt et al. | |

FOREIGN PATENT DOCUMENTS

| | | | | |
|---|---|---|---|---|
| CN | 116535325 A | 8/2023 | | |
| WO | WO-1999/038499 A2 | 8/1999 | | |
| WO | WO-1999/038502 A1 | 8/1999 | | |
| WO | WO-1999/038503 A1 | 8/1999 | | |
| WO | WO-1999/038504 A1 | 8/1999 | | |
| WO | WO-2009105218 A2 * | 8/2009 | ............ | C07B 59/00 |
| WO | WO-2012/118562 A1 | 9/2012 | | |
| WO | WO-2015095713 A1 * | 6/2015 | ........... | A61K 31/137 |

OTHER PUBLICATIONS

Kushner et al., "Pharmacological uses and perspectives of heavy water and deuterated compounds", Canadian Journal of Physiology and Pharmacology, 1999, 77(2), pp. 79-88. (Year: 1999).*
Harbeson et al., "Deuterium in Drug Discovery and Development", Annual Reports in Med Chem, 46, 2011, pp. 403-417 (Year: 2011).*
Khan et al., "Bupropion hydrochloride", 2016, Profiles of Drug Substances, Excipients, and Related Methodology, 41, pp. 1-30 (Year: 2016).*
Maccaroni et al., "Structural and energetic aspects of a new bupropion hydrochloride polymorph", 2012, Journal of Pharmaceutical and Biomedical Analysis, 60, pp. 65-70 (Year: 2012).*
Baillie, Thomas A. "The Use of Stable Isotopes in Pharmacological Research," *Pharmacol. Rev.* vol. 33, No. 2, 1981, pp. 81-132.
Browne, Thomas R. "Stable Isotope Techniques in Early Drug Development: An Economic Evaluation," *J. Clin Pharmacol.* vol. 38, Issue 3, 1998, pp. 213-220.
D'Acquarica et al. "The Quest for Secondary Pharmaceuticals: Drug Repurposing/Chiral-Switches Combination Strategy," *ACS Pharmacol. Transl. Sci.* 2023, vol. 6, No. 2, pp. 201-219.
DeWitt et al. "Deuterium-Enabled Chiral Switching (DECS) Yields Chirally Pure Drugs from Chemically Interconverting Racemates," *ACS Med. Chem. Lett.* 11, 2020, pp. 1789-1792.
Di Martino et al. "Deuterium in drug discovery: progress, opportunities and challenges" *Nature Reviews Drug Discovery*, vol. 22, 2023, pp. 562-584.
Dolan et al. "Discriminative Stimulus and Locomotor Effects of *Para*-Substituted and Benzofuran Analogs of Amphetamine" *Drug Alcohol Depend.* vol. 180, 2017, pp. 39-45.
Dyck et al. "Effects of Deuterium Substitution on the Catabolismof β-Phenylethylamine: An In Vivo Study" *J. Neurochem.* vol. 46, No. 2., 1986, pp. 399-404.
Foris, Anthony "On NH NMR Chemical Shifts" Part I, 2016, pp. 1-74.
Gadde et al. "Bupropion for weight reduction," *Expert Review of Neurotherapeutics*, 2007, 7(1) pp. 17-23.
Gouyette, Alain "Synthesis of Deuterium-labelled Elliptinium and its Use in Metabolic Studies" *Biomedical and Environmental Mass Spectrometry*, vol. 15, 1988, pp. 243-247.
Harbeson et al. "Deuterium in Drug Discovery and Development" *Annual Reports in Med Chem*, 46, 2011, pp. 403-417.
Haskins, N. J. "The Application of Stable Isotopes in Biomedical Research," *Biomedical Mass Spectrometry*, 9(7), 1982, pp. 269-277.
International Search Report and Written Opinion for PCT/US2014/071519, mailed Feb. 10, 2015 (13 pages).
Ishak et al. "The Role of Dopaminergic Agents in Improving Quality of Life in Major Depressive Disorder" *Current Psychiatry Reports*, 11, 2009, pp. 503-508.
Kazuhiko Nakayama "Mechanism of action of new generation antidepressants under development in Japan: Focusing on dopamine neurotransmission" 2009, 29(3) (English Translation of Abstract).

(Continued)

*Primary Examiner* — Bruck Kifle
*Assistant Examiner* — Madeline E Braun
(74) *Attorney, Agent, or Firm* — Goodwin Procter LLP

(57) ABSTRACT

The present disclosure provides a crystalline form of enantiopure deuterium-enriched bupropion, pharmaceutical compositions, and methods of treating mood disorders, neurological disorders, movement disorders, cardiovascular disorders, metabolic disorders, and other disorders using a crystalline form of enantiopure deuterium-enriched bupropion.

15 Claims, 5 Drawing Sheets

(56) References Cited

OTHER PUBLICATIONS

Kushner et al. "Pharmacological uses and perspectives of heavy water and deuterated compounds" *Canadian Journal of Physiology and Pharmacology*, 1999, 77(2), pp. 79-88.
Liu et al. "A Decade of Deuteration in Medicinal Chemistry" *Annual Reports in Medicinal Chemistry*, vol. 50, 2017, pp. 519-542.
Marriott et al. "Pharmaceutical Compounding and Dispending" Second Edition, Pharmaceutical Press, 2010, pp. 1-288.
McConathy et al. "Stereochemistry in Drug Action," Primary Care Companion, *J. Clin. Psychiatry*, 5, 2003, pp. 70-73.
Merz et al. "Deuterium Perturbs the Molecular Arrangement in the Solid State" *Cryst. Growth Des.* 2015, 15, pp. 1553-1558.
Pirali et al. "Applications of Deuterium in Medicinal Chemistry" *J. Med. Chem.* 2019, 62, pp. 5276-5297.
Scheiner et al. "Relative Stability of Hydrogen and Deuterium Bonds" *J. Am. Chem. Soc.* 1996, 118, pp. 1511-1521.
Shao et al. "The Kinetic Isotope Effect in the Search for Deuterated Drugs," *Drug News & Perspectives*, 2010, vol. 23, No. 6, pp. 398-404.
Stotz et al. "Psychostimulants in the therapy of treatment-resistant depression," *Dialogues in Clinical Neuroscience*, 1999, 1(3) pp. 165-174.
Tonn et al. "Simultaneous Analysis of Diphenhydramine and a Stable Isotope Analog (2H10)Diphenydramine Using Capillary Gas Chromatography with Mass Selective Detection in Biological Fluids from Chronically Instrumented Pregnant Ewes," *Biological Mass Spectrometry*, 22(11) 1993, pp. 633-642.
Wolen, R. L. "The application of stable isotopes to studies of drug bioavailability and bioequivalence," *J. Clin. Pharm.* (1986) vol. 26, Abstract only.
*Grunenthal GMBH* vs. *Alkem Laboratories Limited*, 919 F.3d 1333 (2019), 10 pages.
Maccaroni, E. et al., "Structures from powders: Bupropion hydrochloride" J. Pharm. Biomed. Anal. 2009, 50, 257-61.
*Pharmacyclics LLC* v. *Alvogen, Inc.*, 2022 WL 16943006 (11 pages).
Vladiskovic, C. et al. "Persistency of a Two-Fold Embrace in Crystalline Phases of Bupropion Hydrohalides: A Thorough ab Initio X-ray Powder Diffraction Study" Cryst. Growth Des. 2014, 14, 3603-11.

\* cited by examiner

SOLID FORMS OF ENANTIOPURE DEUTERIUM-ENRICHED BUPROPION AND METHODS OF USE THEREOF

TECHNICAL FIELD

The present disclosure provides enantiopure deuterium-enriched bupropion, pharmaceutical compositions, and methods of treating mood disorders, neurological disorders, movement disorders, cardiovascular disorders, metabolic disorders, and other disorders using enantiopure deuterium-enriched bupropion.

BACKGROUND

A large number of mental health, neuropsychiatric, and neurological disorders are linked to dysfunction of one or more neurotransmitter (e.g., dopamine, norepinephrine, and acetylcholine) systems. One class of such medical disorders is mood disorders, such as major depressive disorder, treatment-resistant depression, and seasonal affective disorder, where dysfunction of the dopamine, norepinephrine, and/or acetylcholine systems have been shown to play a significant role. Other medical disorders affected by the dysfunction of the dopamine, norepinephrine, and/or acetylcholine systems include neurological disorders, such as Parkinson's disease, attention deficit hyperactivity disorder, restless legs syndrome, and sexual dysfunction. Dysfunction of the dopamine system has also been linked to drug addiction. For example, drugs such as cocaine and amphetamine have been reported to amplify the effects of dopamine. The dopamine system also has an impact on patients' cognitive function. Too little dopamine or too much dopamine has been reported to impair cognitive function, such as working memory and attention.

Therapeutics have been commercialized for treating disorders associated with dysfunction of neurotransmitter systems. One such example is bupropion hydrochloride, which has been approved by the United States Food and Drug Administration for the treatment of depression and seasonal affective disorder, and as an aid for smoking cessation. Bupropion hydrochloride is marketed under the registered trademark WELLBUTRIN® and Zyban® and the prescribing information for WELLBUTRIN® explains that bupropion is an inhibitor of neuronal uptake of norepinephrine and dopamine. It is also reported that bupropion is a functional antagonist of nicotinic acetylcholine receptor subtypes such as α3, α4β2, α4β3, α3β4, and α1 and that inhibition at these receptors may affect bupropion pharmacological activity. Furthermore, bupropion has been reported to act as a cytochrome-P450 2D6 inhibitor. This characteristic may be useful in modulating exposure to CYP2D6 substrates in combination therapies where bupropion and/or the second agent used in combination may provide a benefit. The commercialized form of bupropion hydrochloride is a racemic mixture and multiple dose-dependent adverse side effects have been reported in patients receiving this therapeutic. Exemplary side effects include seizures, agitation, dry mouth, insomnia, headache, migraine, nausea, vomiting, constipation, and tremor.

Due to the increasing number of patients suffering from disorders associated with dysfunction of neurotransmitter systems, and the limitations of existing therapies, such as adverse side effects, there is a need for new therapeutic agents for treating medical disorders associated with such dysfunction. Attention deficit hyperactivity disorder, for example, has been reported to be one of the most common childhood disorders, and the number of children being diagnosed with attention deficit hyperactivity disorder is increasing. Mood disorders could also benefit from improved therapeutic interventions as a large number of patients do not respond to existing therapy. The present disclosure addresses these needs and provides other related advantages.

SUMMARY

The disclosure, in part, provides deuterium enriched compounds which are crystalline deuterium chloride salts of enantiopure deuterium-enriched bupropion, pharmaceutical compositions, and methods of treating mood disorders, neurological disorders, movement disorders, cardiovascular disorders, metabolic disorders, and other medical disorders using the enantiopure deuterium-enriched bupropion. Further, the deuterium-enriched bupropion is provided in enantiomerically pure form. This enantiomerically pure, deuterium-enriched bupropion provides for a better therapeutic agent than non-deuterated bupropion and/or racemic mixtures of deuterium-enriched bupropion.

Accordingly, provided herein, in part, is a crystalline form of a compound represented by Formula (I):

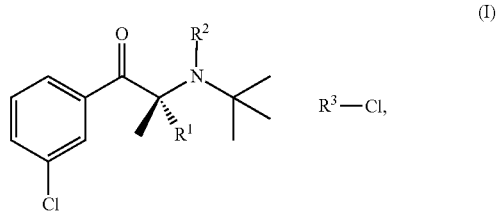

wherein $R^1$, $R^2$, and $R^3$ are each independently H or D, provided that the abundance of deuterium in each of $R^1$, $R^2$, and $R^3$ is at least 30%, and wherein the crystalline form of the compound is characterized by an X-ray powder diffraction pattern comprising peaks at the following diffraction angles (2θ): 12.3°±0.2°, 15.3°±0.2°, and 15.8°±0.2°.

In some embodiments, the crystalline form of the compound is characterized by an X-ray powder diffraction pattern further comprising one or more peaks at the following diffraction angles (2θ): 13.4°±0.2°, 14.1°±0.2°, 16.9°±0.2°, 17.3°±0.2°, 18.4°±0.2°, 18.8°±0.2°, 22.0°±0.2°, and 22.8°±0.2°.

In some embodiments, the crystalline form of the compound is characterized by an X-ray powder diffraction pattern substantially the same as shown in FIG. 3.

In some embodiments, the crystalline form of the compound has a melting point onset as determined by differential scanning calorimetry at about 225° C. to about 235° C.

In some embodiments, the crystalline form of the compound is characterized by a differential scanning calorimetry pattern substantially the same as shown in FIG. 5.

In some embodiments, the crystalline form of the compound is anhydrous.

In some embodiments, the abundance of deuterium in $R^1$ is at least 50%.

In some embodiments, the abundance of deuterium in $R^2$ is at least 50%.

In some embodiments, the abundance of deuterium in $R^3$ is at least 50%.

In some embodiments, the abundance of deuterium in each of $R^1$, $R^2$, and $R^3$ is at least 50%.

In some embodiments, the abundance of deuterium in each of $R^1$, $R^2$, and $R^3$ is at least 75%.

In some embodiments, the abundance of deuterium in each of $R^1$, $R^2$, and $R^3$ is at least 90%.

In some embodiments, the abundance of deuterium in each of $R^1$, $R^2$, and $R^3$ is at least 95%.

In some embodiments, the crystalline form of the compound is characterized by a stereochemical purity of at least 75% enantiomeric excess at the carbon bearing variable $R^1$.

In some embodiments, the crystalline form of the compound is characterized by a stereochemical purity of at least 90% enantiomeric excess at the carbon bearing variable $R^1$.

In some embodiments, the crystalline form of the compound is characterized by a stereochemical purity of at least 95% enantiomeric excess at the carbon bearing variable $R^1$.

Also provided herein is a pharmaceutical composition comprising a crystalline form of the compound represented by Formula (I), and a pharmaceutically acceptable excipient.

The deuterium-enriched compounds disclosed herein are particularly useful in the treatment of medical disorders. Exemplary medical disorders include, for example, mood disorders such as depression, neurological disorders, movement disorders, cardiovascular disorders, and metabolic disorders. The compounds disclosed herein are typically administered to a patient in the form of a pharmaceutical composition. Particularly preferred medical disorders include, for example, depression, obesity, sexual dysfunction, neuropathic pain, attention deficit disorder, attention deficit hyperactivity disorder, and Parkinson's disease. Additional preferred medical disorders include, for example, seasonal affective disorder and depression, e.g., in a patient suffering from Parkinson's disease, and treatment-resistant depression.

Accordingly, one aspect of the disclosure provides a method of treating a disorder selected from the group consisting of depression, obesity, sexual dysfunction, neuropathic pain, attention deficit disorder, attention deficit hyperactivity disorder, and Parkinson's disease. In some embodiments, the disorder is depression. In some embodiments, the disorder is selected from the group consisting of seasonal affective disorder and depression, e.g., in a patient suffering from Parkinson's disease, and treatment-resistant depression. The method comprises administering to a patient in need thereof a therapeutically effective amount of a deuterium-enriched compound described herein, such as a crystalline form of a compound of Formula (I), to treat the disorder. In certain embodiments, the deuterium-enriched compound is a crystalline form of a compound of Formula (I).

Another aspect of the disclosure provides a method of treating a mood disorder selected from the group consisting of clinical depression, major depressive disorder, postnatal depression, postpartum depression, atypical depression, melancholic depression, psychotic major depression, catatonic depression, seasonal affective disorder, dysthymia, double depression, depressive personality disorder, recurrent brief depression, minor depressive disorder, bipolar disorder or manic depressive disorder, depression caused by chronic medical conditions, treatment-resistant depression, refractory depression, anhedonia, and suicidality, suicidal ideation, or suicidal behavior. The method comprises administering to a patient in need thereof a therapeutically effective amount of a deuterium-enriched compound described herein, such as a crystalline form of a compound of Formula (I), to treat the disorder. In certain embodiments, the deuterium-enriched compound is a crystalline form of a compound of Formula (I).

Another aspect of the disclosure provides a method of treating a neurological disorder selected from the group consisting of Alzheimer's disease, tardive dyskinesia, Tourette syndrome, Huntington's disease, Rett syndrome, Prader-Willi syndrome, restless leg syndrome, narcolepsy, ataxia, corticobasal ganglionic degeneration dyskinesia, dystonia, treriors, multiple system atrophy, progressive supranuclear palsy, olivopontocerebellar atrophy, diffuse Lewy body disease, stiff man syndrome, apathy, generalized anxiety, panic disorder, addiction, bipolar disorder, social anxiety disorder, obsessive compulsive disorder, post-traumatic stress disorder, a sleep disorder, an eating disorder, a neuropathic condition, diabetic neuropathy, a cognitive disorder, a psychotic disorder, psychosexual dysfunction, prostate hypertrophy, migraine, bipolar depression, depression in a patient suffering from Alzheimer's disease, depression in a patient suffering from dementia, and depression in a patient suffering from hypothyroidism. The method comprises administering to a patient in need thereof a therapeutically effective amount of a deuterium-enriched compound described herein, such as a crystalline form of a compound of Formula (I), to treat the disorder. In certain embodiments, the deuterium-enriched compound is a crystalline form of a compound of Formula (I).

Another aspect of the disclosure provides a method of treating a movement disorder selected from the group consisting of hereditary spastic paraplegia, myoclonus, spasticity, chorea, athetosis, ballism, stereotypy, tardive dyskinesia, tardive dystonia, tics, hemiballismus, hemi-facial spasm, psychomotor retardation, painful legs and moving toes syndrome, a gait disorder, and a drug-induced movement disorder. The method comprises administering to a patient in need thereof a therapeutically effective amount of a deuterium-enriched compound described herein, such as a crystalline form of a compound of Formula (I), to treat the disorder. In certain embodiments, the deuterium-enriched compound is a crystalline form of a compound of Formula (I).

Another aspect of the disclosure provides a method of treating a disorder selected from the group consisting of inflammatory bowel disease, psoriasis, hypotension, presyncope, syncope, Wilson's disease, shift work sleep disorder, akinetic mutisrn, chronic fatigue syndrome, fibromyalgia, premenstrual syndrome, premenstrual dysphoric disorder, pain, a viral infection, a cardiovascular disease, hepatic steatosis, diabetes, insulin resistance, sleep apnea, arthritis, vascular dementia, gout, calculi, and a disorder requiring a stimulant effect. The method comprises administering to a patient in need thereof a therapeutically effective amount of a deuterium-enriched compound described herein, such as a crystalline form of a compound of Formula (I), to treat the disorder. In certain embodiments, the deuterium-enriched compound is a crystalline form of a compound of Formula (I).

Another aspect of the disclosure provides a method of reducing substance dependence in a patient selected from the group consisting of dependence on an opioid, a nicotine, an amphetamine, a tropane alkaloid, a hypnotic, a depressant, a hallucinogen, and combinations thereof. The method comprises administering to a patient in need thereof a therapeutically effective amount of a deuterium-enriched compound described herein, such as a crystalline form of a compound of Formula (I), to reduce said substance dependence. In certain embodiments, the deuterium-enriched compound is a crystalline form of a compound of Formula (I).

BRIEF DESCRIPTION OF THE DRAWINGS

FIG. 6 is an exemplary microscope image of bupropion HCl.

FIG. 7 is an exemplary microscope image of Compound 101.

DETAILED DESCRIPTION

Figure 1:
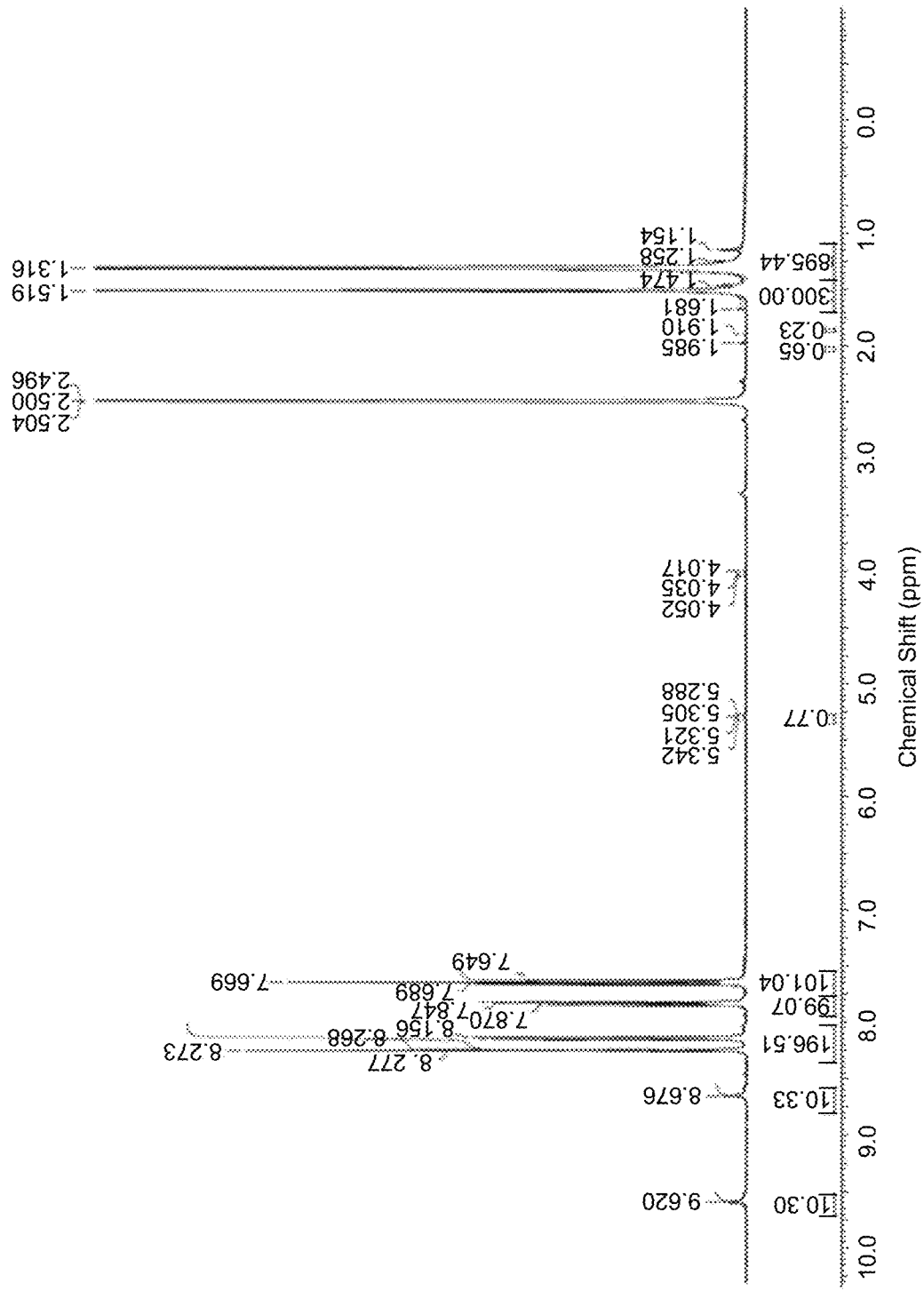
FIG. 1 is an exemplary $^1$H-NMR spectrum of Compound 101.

The present disclosure provides enantiopure deuterium-enriched bupropion, pharmaceutical compositions, and methods of treating mood disorders, neurological disorders, movement disorders, cardiovascular disorders, metabolic disorders, and other medical disorders using enantiopure deuterium-enriched bupropion. Deuterium-enriched refers to the feature that the compound has a quantity of deuterium that is greater than in naturally occurring compounds or synthetic compounds prepared from substrates having the naturally occurring distribution of isotopes. The threshold amount of deuterium enrichment is specified in certain instances in this disclosure, and all percentages given for the amount of deuterium present are mole percentages.

Deuterium ($^2$H) is a stable, non-radioactive isotope of $^1$H hydrogen and has an atomic weight of 2.014. Hydrogen naturally occurs as a mixture of the isotopes $^1$H hydrogen (i.e., protium), deuterium ($^2$H), and tritium ($3$H). The natural abundance of deuterium is 0.015%. One of ordinary skill in the art recognizes that in all chemical compounds with an H atom, the H atom actually represents a mixture of $^1$H hydrogen, deuterium ($^2$H), and tritium ($3$H), where about 0.015% is deuterium. Thus, compounds with a level of deuterium that has been enriched to be greater than its natural abundance of 0.015% are considered unnatural and, as a result, novel over their non-enriched counterparts.

The deuterium-enriched bupropion described herein contains deuterium enrichment at the chiral center of bupropion and optionally in other locations in the compound. Deuterium-enrichment at the chiral center reduces the rate at which the two enantiomers of bupropion may interconvert. Further, the deuterium-enriched bupropion described herein is provided in enantiomerically pure form. This enantiomerically pure, deuterium-enriched bupropion provides for a better therapeutic agent than non-deuterated bupropion and/or racemic mixtures of the compound.

Exemplary compositions and methods of the present disclosure are described in more detail in the following sections: I. Deuterium-Enriched Bupropion; II. Therapeutic Applications; III. Dosing Considerations and Combination Therapy; and IV. Pharmaceutical Compositions. Aspects of the disclosure described in one particular section are not to be limited to any particular section.

I. Deuterium-Enriched Bupropion

One aspect of the disclosure provides deuterium-enriched compounds for use in the therapeutic methods and pharmaceutical compositions described herein. The deuterium-enriched compounds are provided in high enantiomeric purity in order to maximize therapeutic benefit, such as maximal potency per dose of therapeutic agent and minimize adverse side effects, such as seizures.

In one aspect, provided herein is a crystalline form of a compound represented by Formula (I):

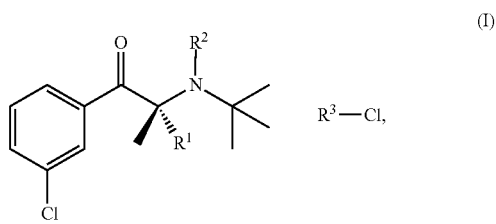

wherein $R^1$, $R^2$, and $R^3$ are each independently H or D, provided that the abundance of deuterium in each of $R^1$, $R^2$, and $R^3$ is at least 30%, and wherein the crystalline form of the compound is characterized by an X-ray powder diffraction pattern comprising one or more peaks at the following diffraction angles (2θ): 12.3°±0.2°, 15.3°±0.2°, and 15.8°±0.2°.

In some embodiments, the crystalline form of the compound is characterized by an X-ray powder diffraction pattern comprising a peak at the following diffraction angle (2θ): 12.3°±0.2°. In some embodiments, the crystalline form of the compound is characterized by an X-ray powder diffraction pattern comprising a peak at the following diffraction angle (2θ): 15.3°±0.2°. In some embodiments, the crystalline form of the compound is characterized by an X-ray powder diffraction pattern comprising a peak at the following diffraction angle (2θ): 15.8°±0.2°. In some embodiments, the crystalline form of the compound is characterized by an X-ray powder diffraction pattern comprising peaks at the following diffraction angles (2θ): 12.3°±0.2°, 15.3°±0.2°, and 15.8°±0.2°.

In some embodiments, the crystalline form of the compound is characterized by an X-ray powder diffraction pattern further comprising one or more peaks at the following diffraction angles (2θ): 13.4°±0.2°, 14.1°±0.2°, 16.9°±0.2°, 17.3°±0.2°, 18.4°±0.2°, 18.8°±0.2°, 22.0°±0.2°, and 22.8°±0.2°. In some embodiments, the crystalline form of the compound is characterized by an X-ray powder diffraction pattern further comprising at least one peak at the following diffraction angles (2θ): 13.4°±0.2°, 14.1°±0.2°, 16.9°±0.2° 17.3°±0.2°, 18.4°±0.2°, 18.8°±0.2°, 22.0°±0.2°, and 22.8°±0.2°. In some embodiments, the crystalline form of the compound is characterized by an X-ray powder diffraction pattern further comprising at least two peaks at the following diffraction angles (2θ): 13.4°±0.2°, 14.1°±0.2°, 16.9°±0.2°, 17.3°±0.2°, 18.4°±0.2°, 18.8°±0.2°, 22.0° 0.2°, and 22.8°±0.2°. In some embodiments, the crystalline form of the compound is characterized by an X-ray powder diffraction pattern further comprising at least three peaks at the following diffraction angles (2θ): 13.4°±0.20°, 14.1°±0.2°, 16.9°±0.2°, 17.3°±0.2°, 18.4°±0.2°, 18.8°±0.2°, 22.0°±0.2°, and 22.8°±0.2°. In some embodiments, the crystalline form of the compound is characterized by an X-ray powder diffraction pattern further comprising peaks at the following diffraction angles (2θ): 13.4°±0.2°, 14.1°±0.2°, 16.9°±0.2° 17.3°±0.2° 18.4°±0.2° 18.8°±0.2°, 22.0°±0.2°, and 22.8°±0.2°.

Figure 3:
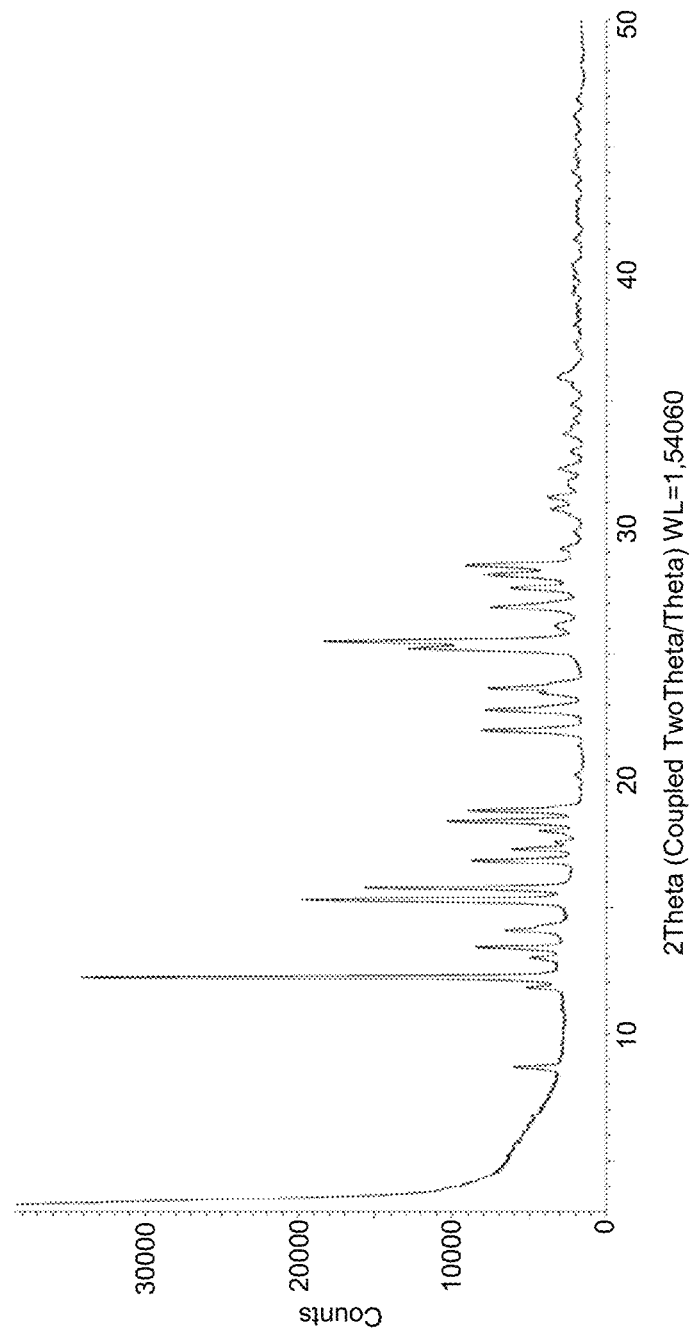
FIG. 3 is an exemplary XRPD pattern of Compound 101.

In some embodiments, the crystalline form of the compound is characterized by an X-ray powder diffraction pattern substantially the same as shown in FIG. 3.

In some embodiments, the crystalline form of the compound has a melting point onset as determined by differential scanning calorimetry at about 225° C. to about 235° C.

Figure 5:
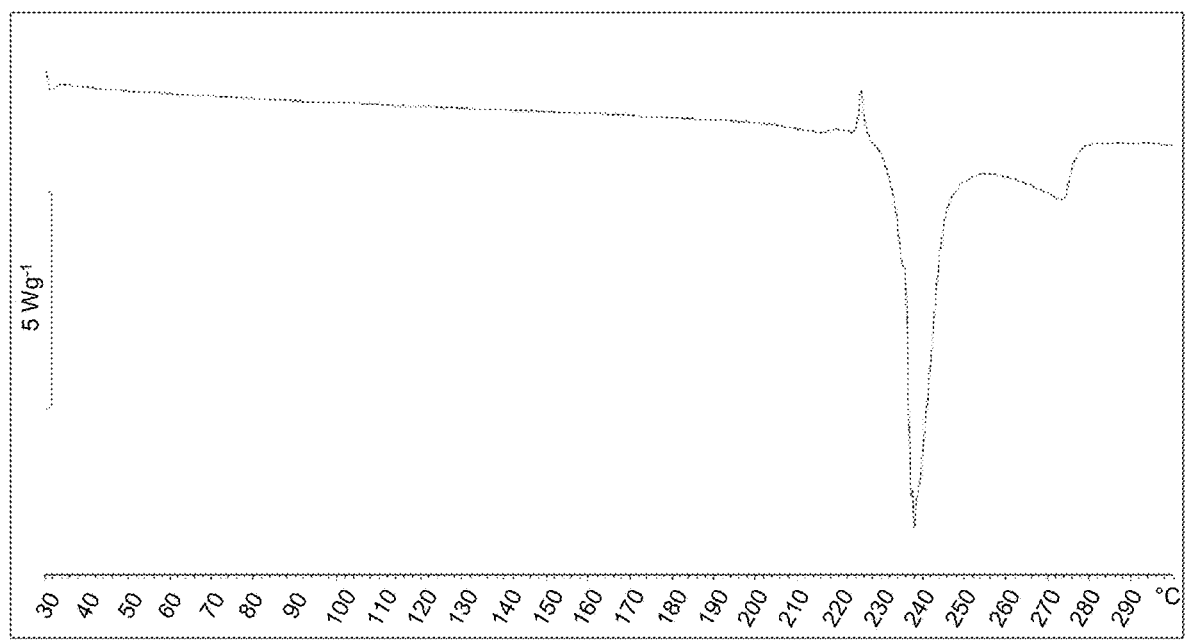
FIG. 5 is an exemplary DSC pattern of Compound 101.

In some embodiments, the crystalline form of the compound is characterized by a differential scanning calorimetry pattern substantially the same as shown in FIG. 5.

In some embodiments, the crystalline form of the compound is anhydrous.

In some embodiments, the abundance of deuterium in $R^1$ is at least 30%. In some embodiments, the abundance of deuterium in $R^1$ is at least 35%. In some embodiments, the abundance of deuterium in $R^1$ is at least 40%. In some embodiments, the abundance of deuterium in $R^1$ is at least 45%. In some embodiments, the abundance of deuterium in $R^1$ is at least 50%. In some embodiments, the abundance of deuterium in $R^1$ is at least 55%. In some embodiments, the abundance of deuterium in $R^1$ is at least 60%. In some embodiments, the abundance of deuterium in $R^1$ is at least 65%. In some embodiments, the abundance of deuterium in $R^1$ is at least 70%. In some embodiments, the abundance of deuterium in $R^1$ is at least 75%. In some embodiments, the abundance of deuterium in $R^1$ is at least 80%. In some embodiments, the abundance of deuterium in $R^1$ is at least 85%. In some embodiments, the abundance of deuterium in $R^1$ is at least 90%. In some embodiments, the abundance of deuterium in $R^1$ is at least 95%. In some embodiments, the abundance of deuterium in $R^1$ is at least 98%. In some embodiments, the abundance of deuterium in $R^1$ is at least 99%. In some embodiments, the abundance of deuterium in $R^1$ is at least 80, 81, 82, 83, 84, 85, 86, 87, 88, 89, 90, 91, 92, 93, 94, 95, 96, 97, 98, or 99%.

In some embodiments, the abundance of deuterium in $R^2$ is at least 30%. In some embodiments, the abundance of deuterium in $R^2$ is at least 35%. In some embodiments, the abundance of deuterium in $R^2$ is at least 40%. In some embodiments, the abundance of deuterium in $R^2$ is at least 45%. In some embodiments, the abundance of deuterium in $R^2$ is at least 50%. In some embodiments, the abundance of deuterium in $R^2$ is at least 55%. In some embodiments, the abundance of deuterium in $R^2$ is at least 60%. In some embodiments, the abundance of deuterium in $R^2$ is at least 65%. In some embodiments, the abundance of deuterium in $R^2$ is at least 70%. In some embodiments, the abundance of deuterium in $R^2$ is at least 75%. In some embodiments, the abundance of deuterium in $R^2$ is at least 80%. In some embodiments, the abundance of deuterium in $R^2$ is at least 85%. In some embodiments, the abundance of deuterium in $R^2$ is at least 90%. In some embodiments, the abundance of deuterium in $R^2$ is at least 95%. In some embodiments, the abundance of deuterium in $R^2$ is at least 98%. In some embodiments, the abundance of deuterium in $R^2$ is at least 99%. In some embodiments, the abundance of deuterium in $R^2$ is at least 80, 81, 82, 83, 84, 85, 86, 87, 88, 89, 90, 91, 92, 93, 94, 95, 96, 97, 98, or 99%.

In some embodiments, the abundance of deuterium in $R^3$ is at least 30%. In some embodiments, the abundance of deuterium in $R^3$ is at least 35%. In some embodiments, the abundance of deuterium in $R^3$ is at least 40%. In some embodiments, the abundance of deuterium in $R^3$ is at least 45%. In some embodiments, the abundance of deuterium in $R^3$ is at least 50%. In some embodiments, the abundance of deuterium in $R^3$ is at least 55%. In some embodiments, the abundance of deuterium in $R^3$ is at least 60%. In some embodiments, the abundance of deuterium in $R^3$ is at least 65%. In some embodiments, the abundance of deuterium in $R^3$ is at least 70%. In some embodiments, the abundance of deuterium in $R^3$ is at least 75%. In some embodiments, the abundance of deuterium in $R^3$ is at least 80%. In some embodiments, the abundance of deuterium in $R^3$ is at least 85%. In some embodiments, the abundance of deuterium in $R^3$ is at least 90%. In some embodiments, the abundance of deuterium in $R^3$ is at least 95%. In some embodiments, the abundance of deuterium in $R^3$ is at least 98%. In some embodiments, the abundance of deuterium in $R^3$ is at least 99%. In some embodiments, the abundance of deuterium in $R^3$ is at least 80, 81, 82, 83, 84, 85, 86, 87, 88, 89, 90, 91, 92, 93, 94, 95, 96, 97, 98, or 99%.

In some embodiments and the abundance of deuterium in $R^1$ and $R^2$ is at least 30%. In some embodiments and the abundance of deuterium in $R^1$ and $R^2$ is at least 35%. In some embodiments and the abundance of deuterium in $R^1$ and $R^2$ is at least 40%. In some embodiments and the abundance of deuterium in $R^1$ and $R^2$ is at least 45%. In some embodiments and the abundance of deuterium in $R^1$ and $R^2$ is at least 50%. In some embodiments and the abundance of deuterium in $R^1$ and $R^2$ is at least 55%. In some embodiments and the abundance of deuterium in $R^1$ and $R^2$ is at least 60%. In some embodiments and the abundance of deuterium in $R^1$ and $R^2$ is at least 65%. In some embodiments and the abundance of deuterium in $R^1$ and $R^2$ is at least 70%. In some embodiments and the abundance of deuterium in $R^1$ and $R^2$ is at least 75%. In some embodiments and the abundance of deuterium in $R^1$ and $R^2$ is at least 80%. In some embodiments and the abundance of deuterium in $R^1$ and $R^2$ is at least 85%. In some embodiments and the abundance of deuterium in $R^1$ and $R^2$ is at least 90%. In some embodiments and the abundance of deuterium in $R^1$ and $R^2$ is at least 95%. In some embodiments and the abundance of deuterium in $R^1$ and $R^2$ is at least 98%. In some embodiments and the abundance of deuterium in $R^1$ and $R^2$ is at least 99%. In some embodiments and the abundance of deuterium in $R^1$ and $R^2$ is at least 80 and 81 and 82 and 83 and 84 and 85 and 86 and 87 and 88 and 89 and 90 and 91 and 92 and 93 and 94 and 95 and 96 and 97 and 98 and or 99%.

In some embodiments, the abundance of deuterium in $R^1$ and $R^3$ is at least 30%. In some embodiments, the abundance of deuterium in $R^1$ and $R^3$ is at least 35%. In some embodiments, the abundance of deuterium in $R^1$ and $R^3$ is at least 40%. In some embodiments, the abundance of deuterium in $R^1$ and $R^3$ is at least 45%. In some embodiments, the abundance of deuterium in $R^1$ and $R^3$ is at least 50%. In some embodiments, the abundance of deuterium in $R^1$ and $R^3$ is at least 55%. In some embodiments, the abundance of deuterium in $R^1$ and $R^3$ is at least 60%. In some embodiments, the abundance of deuterium in $R^1$ and $R^3$ is at least 65%. In some embodiments, the abundance of deuterium in $R^1$ and $R^3$ is at least 70%. In some embodiments, the abundance of deuterium in $R^1$ and $R^3$ is at least 75%. In some embodiments, the abundance of deuterium in $R^1$ and $R^3$ is at least 80%. In some embodiments, the abundance of deuterium in $R^1$ and $R^3$ is at least 85%. In some embodiments, the abundance of deuterium in $R^1$ and $R^3$ is at least 90%. In some embodiments, the abundance of deuterium in $R^1$ and $R^3$ is at least 95%. In some embodiments, the abundance of deuterium in $R^1$ and $R^3$ is at least 98%. In some embodiments, the abundance of deuterium in $R^1$ and $R^3$ is at least 99%. In some embodiments, the abundance of deuterium in $R^1$ and $R^3$ is at least 80, 81, 82, 83, 84, 85, 86, 87, 88, 89, 90, 91, 92, 93, 94, 95, 96, 97, 98, or 99%.

In some embodiments, the abundance of deuterium in $R^2$ and $R^3$ is at least 30%. In some embodiments, the abundance of deuterium in $R^2$ and $R^3$ is at least 35%. In some embodiments, the abundance of deuterium in $R^2$ and $R^3$ is at least 40%. In some embodiments, the abundance of deuterium in $R^2$ and $R^3$ is at least 45%. In some embodiments, the abundance of deuterium in $R^2$ and $R^3$ is at least 50%. In some embodiments, the abundance of deuterium in $R^2$ and $R^3$ is at least 55%. In some embodiments, the abundance of deuterium in $R^2$ and $R^3$ is at least 60%. In some embodiments, the abundance of deuterium in $R^2$ and $R^3$ is at least 65%. In some embodiments, the abundance of deuterium in $R^2$ and $R^3$ is at least 70%. In some embodiments, the abundance of deuterium in $R^2$ and $R^3$ is at least 75%. In some embodiments, the abundance of deuterium in $R^2$ and $R^3$ is at least 80%. In some embodiments, the abundance of deuterium in $R^2$ and $R^3$ is at least 85%. In some embodiments, the abundance of deuterium in $R^2$ and $R^3$ is at least 90%. In some embodiments, the abundance of deuterium in $R^2$ and $R^3$ is at least 95%. In some embodiments, the abundance of deuterium in $R^2$ and $R^3$ is at least 98%. In some embodiments, the abundance of deuterium in $R^2$ and $R^3$ is at least 99%. In some embodiments, the abundance of deuterium in $R^2$ and $R^3$ is at least 80, 81, 82, 83, 84, 85, 86, 87, 88, 89, 90, 91, 92, 93, 94, 95, 96, 97, 98, or 99%.

In some embodiments, the abundance of deuterium in $R^1$, $R^2$, and $R^3$ is at least 30%. In some embodiments, the abundance of deuterium in $R^1$, $R^2$, and $R^3$ is at least 35%. In some embodiments, the abundance of deuterium in $R^1$, $R^2$, and $R^3$ is at least 40%. In some embodiments, the abundance of deuterium in $R^1$, $R^2$, and $R^3$ is at least 45%. In some embodiments, the abundance of deuterium in $R^1$, $R^2$, and $R^3$ is at least 50%. In some embodiments, the abundance of deuterium in $R^1$, $R^2$, and $R^3$ is at least 55%. In some embodiments, the abundance of deuterium in $R^1$, $R^2$, and $R^3$ is at least 60%. In some embodiments, the abundance of deuterium in $R^1$, $R^2$, and $R^3$ is at least 65%. In some embodiments, the abundance of deuterium in $R^1$, $R^2$, and $R^3$ is at least 70%. In some embodiments, the abundance of deuterium in $R^1$, $R^2$, and $R^3$ is at least 75%. In some embodiments, the abundance of deuterium in $R^1$, $R^2$, and $R^3$ is at least 80%. In some embodiments, the abundance of deuterium in $R^1$, $R^2$, and $R^3$ is at least 85%. In some embodiments, the abundance of deuterium in $R^1$, $R^2$, and $R^3$ is at least 90%. In some embodiments, the abundance of deuterium in $R^1$, $R^2$, and $R^3$ is at least 95%. In some embodiments, the abundance of deuterium in $R^1$, $R^2$, and $R^3$ is at least 98%. In some embodiments, the abundance of deuterium in $R^1$, $R^2$, and $R^3$ is at least 99%. In some embodiments, the abundance of deuterium in $R^1$, $R^2$, and $R^3$ is at least 80, 81, 82, 83, 84, 85, 86, 87, 88, 89, 90, 91, 92, 93, 94, 95, 96, 97, 98, or 99%.

In some embodiments, the crystalline form of the compound is characterized by a stereochemical purity of at least 50% enantiomeric excess at the carbon bearing variable $R^1$. In some embodiments, the crystalline form of the compound is characterized by a stereochemical purity of at least 55% enantiomeric excess at the carbon bearing variable $R^1$. In some embodiments, the crystalline form of the compound is characterized by a stereochemical purity of at least 60% enantiomeric excess at the carbon bearing variable $R^1$. In some embodiments, the crystalline form of the compound is characterized by a stereochemical purity of at least 65% enantiomeric excess at the carbon bearing variable $R^1$. In some embodiments, the crystalline form of the compound is characterized by a stereochemical purity of at least 70% enantiomeric excess at the carbon bearing variable $R^1$. In some embodiments, the crystalline form of the compound is characterized by a stereochemical purity of at least 75% enantiomeric excess at the carbon bearing variable $R^1$. In some embodiments, the crystalline form of the compound is characterized by a stereochemical purity of at least 80% enantiomeric excess at the carbon bearing variable $R^1$. In some embodiments, the crystalline form of the compound is characterized by a stereochemical purity of at least 85% enantiomeric excess at the carbon bearing variable $R^1$. In some embodiments, the crystalline form of the compound is characterized by a stereochemical purity of at least 90% enantiomeric excess at the carbon bearing variable $R^1$. In some embodiments, the crystalline form of the compound is characterized by a stereochemical purity of at least 95% enantiomeric excess at the carbon bearing variable $R^1$. In some embodiments, the crystalline form of the compound is characterized by a stereochemical purity of at least 98% enantiomeric excess at the carbon bearing variable $R^1$. In some embodiments, the crystalline form of the compound is characterized by a stereochemical purity of at least 99% enantiomeric excess at the carbon bearing variable $R^1$. In some embodiments, the crystalline form of the compound is characterized by a stereochemical purity of at least 80, 81, 82, 83, 84, 85, 86, 87, 88, 89, 90, 91, 92, 93, 94, 95, 96, 97, 98, or 99% enantiomeric excess at the carbon bearing variable $R^1$.

In some embodiments, the crystalline form of a compound of formula (I) comprises particles which have a rod crystal shape. In some embodiments, the crystalline form of a compound of formula (I) consists essentially of particles which have a rod crystal shape.

In some embodiments, the crystalline form of a compound of formula (I) comprises particles which have a needle crystal shape. In some embodiments, the crystalline form of a compound of formula (I) consists essentially of particles which have a needle crystal shape.

In some embodiments, the crystalline form of a compound of formula (I) comprises particles which have a particle size distribution which is characterized by a Dv(90) of about 1 μm to about 5000 μm, about 10 μm to about 1000 μm, about 50 μm to about 500 μm, about 100 μm to about 300 μm, about 125 μm to about 225 μm or about 150 μm to about 200 μm. In some embodiments, the crystalline form of a compound of formula (I) consists essentially of particles which have a particle size distribution which is characterized by a Dv(90) of about 1 μm to about 5000 μm, about 10 μm to about 1000 μm, about 50 μm to about 500 μm, about 100 μm to about 300 μm, about 125 μm to about 225 μm or about 150 μm to about 200 μm.

In some embodiments, the crystalline form of a compound of formula (I) comprises particles which have a particle size distribution which is characterized by a Dv(50) of about 0.1 μm to about 500 μm, about 1 μm to about 250 μm, about 5 μm to about 100 μm, about 10 μm to about 50 μm, about 20 μm to about 40 μm or about 25 μm to about 35 μm. In some embodiments, the crystalline form of a compound of formula (I) consists essentially of particles which have a particle size distribution which is characterized by a Dv(50) of about 0.1 μm to about 500 μm, about 1 μm to about 250 μm, about 5 μm to about 100 μm, about 10 μm to about 50 μm, about 20 μm to about 40 μm or about 25 μm to about 35 μm.

In some embodiments, the crystalline form of a compound of formula (I) comprises particles which have a particle size distribution which is characterized by a Dv(10) of about 0.01 μm to about 100 μm, about 0.1 μm to about 50 μm, about 0.5 μm to about 25 μm, about 1 μm to about 15 μm, about 2 μm to about 12 μm or about 5 μm to about 9 μm. In some embodiments, the crystalline form of a compound of formula (I) consists essentially of particles which have a particle size distribution which is characterized by a Dv(10)

of about about 0.01 µm to about 100 µm, about 0.1 µm to about 50 µm, about 0.5 µm to about 25 µm, 1 µm to about 15 µm, about 2 µm to about 12 µm or about 5 µm to about 9 µm.

Compounds described herein can be provided in isolated or purified form. Isolated or purified compounds are a group of compounds that have been separated from their environment, such as from a crude reaction mixture if made in a laboratory setting or removed from their natural environment if naturally occurring. Examples of the purity of the isolated compound include, for example, at least 50%, 55%, 60%, 65%, 70%, 75%, 80%, 85%, 90%, 95%, to 100% by weight. In some embodiments, the purity of the crystalline form of a compound of formula (I) is at least 50% by weight. In some embodiments, the purity of the crystalline form of a compound of formula (I) is at least 55% by weight. In some embodiments, the purity of the crystalline form of a compound of formula (I) is at least 60% by weight. In some embodiments, the purity of the crystalline form of a compound of formula (I) is at least 65% by weight. In some embodiments, the purity of the crystalline form of a compound of formula (I) is at least 70% by weight. In some embodiments, the purity of the crystalline form of a compound of formula (I) is at least 75% by weight. In some embodiments, the purity of the crystalline form of a compound of formula (I) is at least 80% by weight. In some embodiments, the purity of the crystalline form of a compound of formula (I) is at least 85% by weight. In some embodiments, the purity of the crystalline form of a compound of formula (I) is at least 90% by weight. In some embodiments, the purity of the crystalline form of a compound of formula (I) is at least 95% by weight. In some embodiments, the purity of the crystalline form of a compound of formula (I) is at least 98% by weight. In some embodiments, the purity of the crystalline form of a compound of formula (I) is at least 99% by weight.

It is understood that the deuterium-enriched compounds described herein can be combined with a pharmaceutically acceptable carrier to form a pharmaceutical composition.

Another aspect of the disclosure provides a unit quantum of a deuterium-enriched compound described herein, such as an amount of at least (a) one µg of a disclosed deuterium-enriched compound, (b) one mg, or (c) one gram. In further embodiments, the quantum is, for example, at least 0.01, 0.02, 0.03, 0.04, 0.05, 0.1, 0.2, 0.3, 0.4, 0.5, or 1 mole of the compound. The present amounts also cover lab-scale (e.g., gram scale including 1, 2, 3, 4, 5 g, etc.), kilo-lab scale (e.g., kilogram scale including 1, 2, 3, 4, 5 kg, etc.), and industrial or commercial scale (e.g., multi-kilogram or above scale including 100, 200, 300, 400, 500 kg, etc.) quantities as these will be more useful in the actual manufacture of a pharmaceutical. Industrial/commercial scale refers to the amount of product that would be produced in a batch that was designed for clinical testing, formulation, sale/distribution to the public, etc.

Also provided herein is a process of preparing a compound represented by Formula (I):

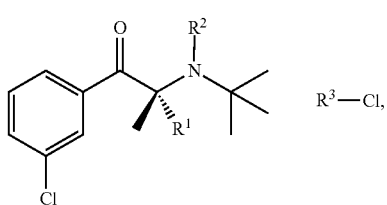

(I)

wherein $R^1$, $R^2$, and $R^3$ are each independently H or D, provided that the abundance of deuterium in $R^1$, $R^2$, and $R^3$ is at least 30%, the process comprising:
i) neutralizing a compound represented by Formula (II):

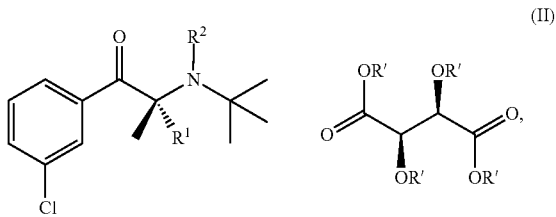

(II)

wherein $R^1$ and $R^2$ are each independently H or D; and each R' is independently H or D, provided that the abundance of deuterium in $R^1$, $R^2$, or at least one of R' is at least 30%, with a base to provide a compound of Formula (III):

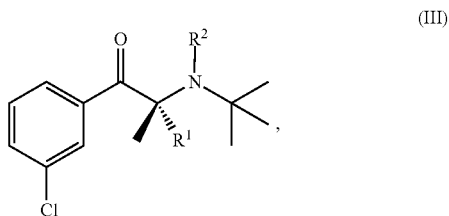

(III)

and
ii) contacting the compound of Formula (III) with chlorotrimethylsilane (TMSCl) to form the compound represented by Formula (I).

In some embodiments, the process comprises contacting the compound represented by Formula (III) with TMSCl in the presence of ethyl acetate. In some embodiments, the contacting occurs at about 5 to about 30° C.

In some embodiments, prior to contacting the compound represented by Formula (III) with TMSCl, the compound represented by Formula (II) is dissolved in $D_2O$ and ethyl acetate to form a mixture. In some embodiments, the process comprises contacting said mixture with the base to form a basic mixture. In some embodiments, the base is potassium carbonate ($K_2CO_3$). In some embodiments, the pH of the basic mixture is adjusted to about 8 to about 12. In some embodiments, the pH of the basic mixture is adjusted to about 8 to about 11. In some embodiments, the pH of the basic mixture is adjusted to about 8.7 to about 10.5. In some embodiments, the pH of the basic mixture is adjusted to about 9.0 to about 10.2. In some embodiments, the pH of the basic mixture is adjusted to about 9.3 to about 9.9. In some embodiments, the pH of the basic mixture is adjusted to about 8.8. In some embodiments, the pH of the basic mixture is adjusted to about 9.0. In some embodiments, the pH of the basic mixture is adjusted to about 9.2. In some embodiments, the pH of the basic mixture is adjusted to about 9.4. In some embodiments, the pH of the basic mixture is adjusted to about 9.6. In some embodiments, the pH of the basic mixture is adjusted to about 9.8. In some embodiments, the pH of the basic mixture is adjusted to about 10.0. In some embodiments, the pH of the basic mixture is adjusted to about 10.2. In some embodiments, the pH of the basic mixture is adjusted to about 10.4. In some embodiments, the neutralizing occurs at less than about 35° C. In some embodiments, the neutralizing occurs at less than about 30° C. In some embodiments, the neutralizing occurs at less than about 25° C. In some embodiments, the neutralizing occurs at about 0 to about 35° C. In some embodiments, the neutralizing occurs at about 0 to about 25° C. In some embodiments, the neutralizing occurs at about 5 to about 35° C. In some embodiments, the neutralizing occurs at about 5 to about 25° C. In some embodiments, the neutralizing occurs at about 10 to about 35° C. In some embodiments, the neutralizing occurs at about 10 to about 25° C. In some embodiments, the process further comprises distilling said basic mixture (e.g., to remove an impurity such as tert-butyl amine L-tartaric acid salt). In some embodiments, the process further comprises adding fresh ethyl acetate after distillation. In some embodiments, the process further comprises separating the ethyl acetate layer from the basic mixture. In some embodiments, the process further comprises washing the ethyl acetate layer with $D_2O$, and optionally back-extracting the $D_2O$ layer with ethyl acetate. In some embodiments, the process further comprises filtering the ethyl acetate layer(s).

In some embodiments, the process after contacting the compound represented by Formula (III) with TMSCl further comprises seeding with a compound of Formula (I). In some embodiments, the process further comprises distillation (e.g., to remove $D_2O$, ethanol, and/or acetic acid.)

In some embodiments, the compound of Formula (I) is crystalline, as described herein.

In some embodiments, the process further comprises:
contacting a compound represented by Formula (IV):

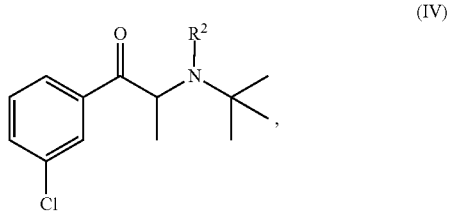

with L-tartaric acid to form the compound represented by Formula (II).

In some embodiments, the process comprises contacting the compound represented by Formula (IV) with L-tartaric acid in the presence of $D_2O$.

In some embodiments, the process comprises contacting the compound represented by Formula (IV) with L-tartaric acid at about 45° C. to about 65° C. In some embodiments, the process comprises contacting the compound represented by Formula (IV) with L-tartaric acid at about 50° C. to about 60° C. In some embodiments, the process comprises contacting the compound represented by Formula (IV) with L-tartaric acid at about 55° C.

In some embodiments, the process further comprises distillation to form a residue. In some embodiments, the process further comprises contacting the residue with additional $D_2O$.

In some embodiments, the process further comprises addition of another solvent, such as acetonitrile. In some embodiments, the process further comprises seeding with a compound of Formula (II), then cooling, down to e.g., about −40 to about 5° C., about −35 to about 0° C., about −35 to about −5° C., about −35 to about −10° C., about −35 to about −15° C., about −30 to about −20° C., or about −28 to about −25° C.

In some embodiments, the process further comprises:
contacting a compound represented by Formula (V):

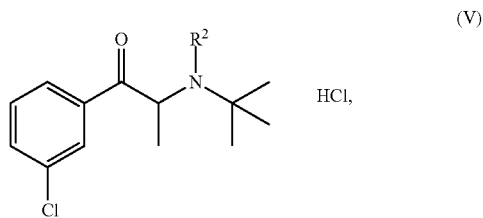

with a base to form the compound represented by Formula (IV).

In some embodiments, the base is $K_2CO_3$. In some embodiments, the contacting occurs in the presence of dichloromethane and water. In some embodiments, the pH of the mixture of the compound of Formula (V), dichloromethane, and water is adjusted to about 8 to about 12. In some embodiments, the pH of the mixture of the compound of Formula (V), dichloromethane, and water is adjusted to about 8 to about 11. In some embodiments, the pH of the mixture of the compound of Formula (V), dichloromethane, and water is adjusted to about 8.8 to about 10.8. In some embodiments, the pH of the mixture of the compound of Formula (V), dichloromethane, and water is adjusted to about 9.2 to about 10.4. In some embodiments, the pH of the mixture of the compound of Formula (V), dichloromethane, and water is adjusted to about 9.5 to about 10.1. In some embodiments, the pH of the mixture of the compound of Formula (V), dichloromethane, and water is adjusted to about 9.0. In some embodiments, the pH of the mixture of the compound of Formula (V), dichloromethane, and water is adjusted to about 9.2. In some embodiments, the pH of the mixture of the compound of Formula (V), dichloromethane, and water is adjusted to about 9.4. In some embodiments, the pH of the mixture of the compound of Formula (V), dichloromethane, and water is adjusted to about 9.6. In some embodiments, the pH of the mixture of the compound of Formula (IV), dichloromethane, and water is adjusted to about 9.8. In some embodiments, the pH of the mixture of the compound of Formula (V), dichloromethane, and water is adjusted to about 9.9. In some embodiments, the pH of the mixture of the compound of Formula (V), dichloromethane, and water is adjusted to about 10.0. In some embodiments, the pH of the mixture of the compound of Formula (V), dichloromethane, and water is adjusted to about 10.2. In some embodiments, the pH of the mixture of the compound of Formula (V), dichloromethane, and water is adjusted to about 10.4. In some embodiments, the pH of the mixture of the compound of Formula (V), dichloromethane, and water is adjusted to about 10.6.

In some embodiments, the process further comprises extracting the compound of Formula (IV) in a solvent (e.g., dichloromethane) at least once (e.g., once, twice, or three times) and concentrating the solvent (e.g., dichloromethane).

II. Therapeutic Applications

The disclosure provides methods of using deuterium-enriched compounds described herein to treat medical disorders. Preferred medical disorders for treatment include mood disorders, neurological disorders, movement disorders, metabolic disorders, and cardiovascular disorders. Use of the deuterium-enriched compounds having high enantiomeric purity is contemplated to maximize therapeutic benefit, such as achieving increased potency per dose of therapeutic agent and minimize adverse side effects. The deuterium-enriched compound can be, for example, a deuterium-enriched compound described in Section I above.

Treating Mood Disorders

Accordingly, one aspect of the disclosure provides a method of treating a mood disorder. Mood disorders include, but are not limited to, clinical depression, postnatal depression, postpartum depression, atypical depression, melancholic depression, psychotic major depression, catatonic depression, seasonal affective disorder, dysthymia, double depression, depressive personality disorder, recurrent brief depression, minor depressive disorder, bipolar disorder or manic depressive disorder, depression caused by chronic medical conditions, treatment-resistant depression, refractory depression, anhedonia, and suicidality, suicidal ideation, or suicidal behavior.

In some embodiments, the mood disorder is selected from the group consisting of seasonal affective disorder, depression in a patient suffering from Parkinson's disease, and treatment-resistant depression.

Clinical depression is also known as major depression, major depressive disorder, severe depression, unipolar depression, unipolar disorder, and recurrent depression, and refers to a mental disorder characterized by pervasive and persistent low mood that is accompanied by low self-esteem and loss of interest or pleasure in normally enjoyable activities. Some people with clinical depression have trouble sleeping, lose weight, and generally feel agitated and irritable. Clinical depression affects how an individual feels, thinks, and behaves and may lead to a variety of emotional and physical problems. Individuals with clinical depression may have trouble doing day-to-day activities and make an individual feel as if life is not worth living.

Postnatal depression (PND) is also referred to as postpartum depression and refers to a type of clinical depression that affects women after childbirth. Symptoms can include sadness, fatigue, changes in sleeping and eating habits, reduced sexual desire, crying episodes, anxiety, and irritability. In some embodiments, the PND is a treatment-resistant depression (e.g., a treatment-resistant depression as described herein). In some embodiments, the PND is refractory depression (e.g., a refractory depression as described herein).

Atypical depression (AD) is characterized by mood reactivity (e.g., paradoxical anhedonia) and positivity, significant weight gain or increased appetite. Patients suffering from AD also may have excessive sleep or somnolence (hypersomnia), a sensation of limb heaviness, and significant social impairment as a consequence of hypersensitivity to perceived interpersonal rejection.

Melancholic depression is characterized by loss of pleasure (anhedonia) in most or all activities, failures to react to pleasurable stimuli, depressed mood more pronounced than that of grief or loss, excessive weight loss, or excessive guilt.

Psychotic major depression or psychotic depression refers to a major depressive episode, in particular of melancholic nature, where the individual experiences psychotic symptoms such as delusions and hallucinations.

Catatonic depression refers to major depression involving disturbances of motor behavior and other symptoms. An individual may become mute and stuporous, and either is immobile or exhibits purposeless or bizarre movements.

Seasonal affective disorder generally refers to the recurrent major depressive disorder that coincides with the seasonal pattern that occurs at a specific time of the year and fully remits otherwise. Patients suffering from seasonal affective disorder may experience difficulty waking up in the morning, morning sickness, tendency to oversleep and overeat, and cravings for carbohydrates. This disorder is sometimes more prevalent in winter months, particularly in geographies that experience reduced daylight hours. Winter seasonal affective disorder is characterized by the onset of depression in the fall or winter followed by recovery in the spring.

Dysthymia refers to a condition related to unipolar depression, where the same physical and cognitive problems are evident. They are not as severe and tend to last longer (e.g., at least 2 years).

Double depression refers to fairly depressed mood (dysthymia) that lasts for at least 2 years and is punctuated by periods of major depression.

Depressive Personality Disorder refers to a personality disorder with depressive features.

Recurrent Brief Depression refers to a condition in which individuals have depressive episodes about once per month, each episode lasting 2 weeks or less and typically less than 2-3 days.

Minor depressive disorder or minor depression refers to a depression in which at least 2 symptoms are present for 2 weeks.

Bipolar disorder or manic depressive disorder causes extreme mood swings that include emotional highs (mania or hypomania) and lows (depression). During periods of mania the individual may feel or act abnormally happy, energetic, or irritable. They often make poorly thought out decisions with little regard to the consequences. The need for sleep is usually reduced. During periods of depression there may be crying, poor eye contact with others, and a negative outlook on life. The risk of suicide among those with the disorder is high at greater than 6% over 20 years, while self-harm occurs in 30-40%. Other mental health issues such as anxiety disorder and substance use disorder are commonly associated with bipolar disorder.

Depression caused by chronic medical conditions refers to depression caused by chronic medical conditions such as cancer or chronic pain, chemotherapy, chronic stress. For example, depression in patients suffering from Parkinson's disease is a frequent complication. The Parkinson's Disease Foundation has reported that up to sixty percent of patients suffering from Parkinson's disease exhibit mild to moderate depression.

Treatment-resistant depression refers to a condition where the individuals have been treated for depression, but the symptoms do not improve. For example, antidepressants or psychological counseling (psychotherapy) do not ease depression symptoms for individuals with treatment-resistant depression. In some cases, symptoms in individuals with treatment-resistant depression improve, but come back.

Refractory depression occurs in patients suffering from depression who are resistant to standard pharmacological treatments, including tricyclic antidepressants, monoamine-oxidase inhibitors, selective serotonin-reuptake inhibitors, and double and triple uptake inhibitors and/or anxiolytic drugs, as well as non-pharmacological treatments (e.g., psychotherapy, electroconvulsive therapy, vagus nerve stimulation, and/or transcranial magnetic stimulation).

Anhedonia generally refers to an inability to experience pleasure from activities usually found enjoyable. The lack of pleasure may have causes that are not due to an underlying disorder or disease. Examples include overwork, recent tragedy, financial problems, bad weather, and boring activities. In other embodiments, anhedonia is associated with an underlying disorder or disease.

Suicidality, suicidal ideation, suicidal behavior refers to the tendency of an individual to commit suicide. Suicidal ideation concerns thoughts about or an unusual preoccupation with suicide. The range of suicidal ideation varies greatly from e.g., fleeting thoughts to extensive thoughts, detailed planning, role playing, incomplete attempts. Symptoms include talking about suicide, getting the means to commit suicide, withdrawing from social contact, being preoccupied with death, feeling trapped or hopeless about a situation, increasing use of alcohol or drugs, doing risky or self-destructive things, saying goodbye to people as if they won't be seen again.

Symptoms of depression include persistent anxious or sad feelings, feelings of helplessness, hopelessness, pessimism, worthlessness, low energy, restlessness, irritability, fatigue, loss of interest in pleasurable activities or hobbies, absence of positive thoughts or plans, excessive sleeping, overeating, appetite loss, insomnia, self-harm, anhedonia, thoughts of suicide, and suicide attempts. The presence, severity, frequency, and duration of symptoms may vary on a case-to-case basis. Symptoms of depression, and relief of the same, may be ascertained by a physician or psychologist (e.g., by a mental state examination).

Thus, the method comprises administering to a patient in need thereof a therapeutically effective amount of a deuterium-enriched compound described herein, such as a crystalline form of a compound of Formula (I), to treat the disorder. In certain embodiments, the deuterium-enriched compound is a crystalline form of a compound of Formula (I).

Treating Obesity

Obesity generally refers to the medical condition in which the patient suffers from excess body fat. Obesity is a leading preventable cause of death worldwide and is considered by various authorities to be a serious public health problem.

Thus, another aspect of the disclosure provides a method of treating obesity. The method comprises administering to a patient in need thereof a therapeutically effective amount of a deuterium-enriched compound described herein, such as a crystalline form of a compound of Formula (I), to treat the disorder. In certain embodiments, the deuterium-enriched compound is a crystalline form of a compound of Formula (I).

Treating Sexual Dysfunction

Sexual dysfunction generally refers to difficulty experienced by an individual during any stage of normal sexual activity, including physical pleasure, desire, preference, arousal, or orgasm. Sexual dysfunction can have a significant impact on an individual's perceived quality of sexual life. The sexual dysfunction can be female sexual dysfunction, which can be characterized by one or more of the following insofar as the event causes distress: hypoactive sexual desire, sexual aversion, sexual arousal disorder, and/or orgasmic disorder. In certain other embodiments, the sexual dysfunction is female hyposexual desire disorder. In yet other embodiments, the sexual dysfunction is male sexual dysfunction, such as premature ejaculation or male hyposexual desire disorder.

Thus, another aspect of the disclosure provides a method of treating sexual dysfunction. The method comprises administering to a patient in need thereof a therapeutically effective amount of a deuterium-enriched compound described herein, such as a crystalline form of a compound of Formula (I), to treat the sexual dysfunction. In certain embodiments, the deuterium-enriched compound is a crystalline form of a compound of Formula (I).

Treating Neuropathic Pain

Neuropathic pain generally refers to pain caused by damage or disease that affects the somatosensory system. Neuropathic pain can result from disorders of the peripheral nervous system or the central nervous system (e.g., brain and spinal cord). A substantial percentage of the population, particularly the European population, suffers from neuropathic pain. The neuropathic pain can be, for example, a postherpetic neuralgia, a trigeminal neuralgia, phantom limb pain, pain associated with diabetic neuropathy, and/or pain associated with carpal tunnel syndrome.

Thus, another aspect of the disclosure provides a method of treating neuropathic pain. The method comprises administering to a patient in need thereof a therapeutically effective amount of a deuterium-enriched compound described herein, such as a crystalline form of a compound of Formula (I), to treat the neuropathic pain. In certain embodiments, the deuterium-enriched compound is a crystalline form of a compound of Formula (I).

Treating Attention Deficit Hyperactivity Disorder

Another aspect of the disclosure provides a method of treating attention deficit disorder such as attention deficit hyperactivity disorder. The method comprises administering to a patient in need thereof a therapeutically effective amount of a deuterium-enriched compound described herein, such as a crystalline form of a compound of Formula (I), to treat the disorder. In certain embodiments, the deuterium-enriched compound is a crystalline form of a compound of Formula (I).

In certain embodiments, the attention deficit disorder is adult attention deficit disorder.

Attention deficit hyperactivity disorder generally refers to the art-recognized condition in which a patient suffers from significant problems of attention and/or hyperactivity and acting impulsively that are not appropriate for a person's age. An increasing number of children are being diagnosed with attention deficit disorder and attention deficit hyperactivity disorder, and a significant percentage of children with attention deficit hyperactivity disorder or attention deficit disorder continue to suffer from the disorder in adulthood.

Facilitating Weight Loss and/or Reducing Cholesterol

Another aspect of the disclosure provides a method of facilitating weight loss in a patient. The method comprises administering to a patient in need thereof a therapeutically effective amount of a deuterium-enriched compound described herein, such as a crystalline form of a compound of Formula (I), to facilitate weight loss. In certain embodiments, the deuterium-enriched compound is a crystalline form of a compound of Formula (I).

In certain embodiments, the method produces at least a 1%, 2%, or 5% reduction in bodyweight of the patient.

Another aspect of the disclosure provides a method of reducing the amount of cholesterol in a patient. The method comprises administering to a patient in need thereof a therapeutically effective amount of a deuterium-enriched compound described herein, such as a crystalline form of a compound of Formula (I), to reduce the amount of cholesterol in the patient. In certain embodiments, the deuterium-enriched compound is a crystalline form of a compound of Formula (I).

Treating Neurological Disorders

Another aspect of the disclosure provides a method of treating a neurological disorder selected from the group consisting of Alzheimer's disease, tardive dyskinesia, Tourette syndrome, Huntington's disease, Rett syndrome, Prader-Willi syndrome, restless leg syndrome, narcolepsy, ataxia, corticobasal ganglionic degeneration dyskinesia, dystonia, tremors, multiple system atrophy, progressive supranuclear palsy, olivopontocerebellar atrophy, diffuse Lewy body disease, stiff man syndrome, apathy, generalized anxiety, panic disorder, addiction, bipolar disorder, social anxiety disorder, obsessive compulsive disorder, post-traumatic stress disorder, a sleep disorder, an eating disorder, a neuropathic condition, diabetic neuropathy, a cognitive disorder, a psychotic disorder, psychosexual dysfunction, prostate hypertrophy, migraine, bipolar depression, depression in a patient suffering from Alzheimer's disease, depression in a patient suffering from dementia, and depression in a patient suffering from hypothyroidism. The method comprises administering to a patient in need thereof a therapeutically effective amount of a deuterium-enriched compound described herein, such as a crystalline form of a compound of Formula (I), to treat the disorder. In certain embodiments, the deuterium-enriched compound is a crystalline form of a compound of Formula (I).

In certain embodiments, the neurological disorder is a sleep disorder, such as hypersomnia and/or sleep apnea.

In certain embodiments, the neurological disorder is a cognitive disorder, such as cognitive impairment and/or memory impairment. The cognitive impairment may be, for example, cognitive impairment associated with attention deficit hyperactivity disorder, Alzheimer's disease, Prader-Willi syndrome, senile dementia, traumatic brain injury, and/or pathogenic brain injury. In certain other embodiments, the neurological disorder is an eating disorder, such as bulimia.

In certain embodiments, the neurological disorder is addiction, such as gambling addiction, sex addiction, or drug addiction, such as addiction to one or more of a stimulant, cocaine, tobacco, an opioid, nicotine, alcohol, an amphetamine, or a psychostimulant. In certain embodiments, the drug addiction is methamphetamine dependence. In yet other embodiments, the drug addiction is an addiction to one or more of an opioid, a stimulant, a hypnotic, a depressant, or a hallucinogen.

Another aspect of the disclosure provides a method of improving cognition in a patient suffering from a neurological disorder, such as Alzheimer's disease, Parkinson's disease, attention deficit hyperactivity disorder, dementia (such as senile dementia), or one of the other neurological disorders described herein. The method comprises administering to a patient in need thereof a therapeutically effective amount of a deuterium-enriched compound described herein, such as a crystalline form of a compound of Formula (I), to improve cognition. In certain embodiments, the deuterium-enriched compound is a crystalline form of a compound of Formula (I).

Treating Substance Use Disorders

Another aspect of the disclosure provides a method of reducing a withdrawal symptom associated with reduced consumption of a substance by a patient. The method comprises administering to a patient in need thereof a therapeutically effective amount of a deuterium-enriched compound described herein, such as a crystalline form of a compound of Formula (I), to reduce the frequency or intensity of a withdrawal symptom associated with reduced consumption of a substance by a patient. The withdrawal symptom may be, for example, anxiety, restlessness, irritability, insomnia, headache, poor concentration, depression, social isolation, sweating, racing heart, palpitations, muscle tension, tightness in the chest, difficulty breathing, tremor, nausea, vomiting, diarrhea, hallucination, stroke, heart attack, and/or grand mal seizure. The drug may be an opioid, a stimulant, a hypnotic, a depressant, or a hallucinogen. In yet other embodiments, the substance may be an opioid (e.g., heroin), an amphetamine stimulant (e.g., methamphetamine or mephedrone), a tropane alkaloid (e.g., cocaine), a hypnotic, a depressant, or a hallucinogen. In certain embodiments, the deuterium-enriched compound is a crystalline form of a compound of Formula (I).

Another aspect of the disclosure provides a method of reducing a rewarding effect of a substance upon consumption of the substance by the patient. The method comprises administering to a patient in need thereof a therapeutically effective amount of a deuterium-enriched compound described herein, such as a crystalline form of a compound of Formula (I), to reduce the reward effect produced by a substance upon consumption of the substance by the patient. The rewarding effect may be, for example, euphoria and/or increased energy. The substance may be an opioid, a stimulant, a hypnotic, a depressant, or a hallucinogen. In yet other embodiments, the substance may be an opioid (e.g., heroin), an amphetamine stimulant (e.g., methamphetamine or mephedrone), a tropane alkaloid (e.g., cocaine), a hypnotic, a depressant, or a hallucinogen. In certain embodiments, the deuterium-enriched compound is a crystalline form of a compound of Formula (I).

Another aspect of the disclosure provides a method of reducing dependence by a patient to a substance selected from the group consisting of an opioid, nicotine, an amphetamine, a tropane alkaloid, a hypnotic, an anti-depressant, a hallucinogen, a pain medication, a sleep medication, and combinations thereof. The method comprises administering to a patient in need thereof a therapeutically effective amount of a deuterium-enriched compound described herein, such as a crystalline form of a compound of Formula (I), to reduce said substance dependence. In certain embodiments, the substance may be an opioid (e.g., heroin or oxycodone), an amphetamine (e.g., methamphetamine or mephedrone), a tropane alkaloid (e.g., cocaine), a hypnotic (e.g., a benzodiazepine), an anti-depressant, or a hallucinogen. In certain embodiments, the substance is methamphetamine or cocaine. In certain embodiments, the deuterium-enriched compound is a crystalline form of a compound of Formula (I). Another aspect of the disclosure provides a method for treating the effects of ethanol consumption in a patient. The method comprises administering to a patient in need thereof a therapeutically effective amount of a deuterium-enriched compound described herein, such as a crystalline form of a compound of Formula (I), to treat the effects of ethanol consumption. In certain embodiments, the deuterium-enriched compound is a crystalline form of a compound of Formula (I).

Treating Movement Disorders

Another aspect of the disclosure provides a method of treating a movement disorder selected from the group consisting of hereditary spastic paraplegia, myoclonus, spasticity, chorea, athetosis, ballism, stereotypy, tardive dyskinesia, tardive dystonia, tics, hemiballismus, hemifacial spasm, psychomotor retardation, painful legs and moving toes syndrome, a gait disorder, and a drug-induced movement disorder. The method comprises administering to a patient in need thereof a therapeutically effective amount of a deuterium-enriched compound described herein, such as a crystalline form of a compound of Formula (I), to treat the disorder. In certain embodiments, the deuterium-enriched compound is a crystalline form of a compound of Formula (I).

Treating Additional Medical Disorders

Another aspect of the disclosure provides a method of treating a disorder selected from the group consisting of inflammatory bowel disease, psoriasis, hypotension, presyncope, syncope, Wilson's disease, shift-work sleep disorder, akinetic mutism, chronic fatigue syndrome, fibromyalgia, premenstrual syndrome, premenstrual dysphoric disorder, pain, a viral infection, a cardiovascular disease (e.g., hypertension, heart failure, dyslipidemia, hypercholesterolemia, hypertriglyceridemia, or hyperlipoproteinemia), hepatic steatosis, diabetes, insulin resistance, sleep apnea, arthritis, vascular dementia, gout, calculi, and a disorder requiring a stimulant effect. The method comprises administering to a patient in need thereof a therapeutically effective amount of a deuterium-enriched compound described herein, such as a crystalline form of a compound of Formula (I), to treat the disorder. In certain embodiments, the deuterium-enriched compound is a crystalline form of a compound of Formula (I).

In certain embodiments, the disorder is pain, such as chronic pain, pain associated with depression, persistent headache, or reflex sympathetic dystrophy. In certain embodiments, the disorder is a cardiovascular disease, such as hypertension, heart failure, dyslipidemia, hypercholesterolemia, hypertriglyceridemia, or hyperlipoproteinemia.

Additional Features of Therapeutic Methods

The therapeutic methods can be further characterized according to blood plasma stability of the deuterated S-enantiomer of bupropion administered to the patient. In certain embodiments, the molar ratio of S-enantiomer to R-enantiomer of bupropion present in the patient's blood plasma measured at 30 minutes (or 1 h 2 h, 3 h, 4 h, 5 h, or 6 h) after administration of the deuterated S-bupropion is within 10% (or 5%, 15%, 20%, 25%, 30%, 35%, 40%, 45%, or 50%) of the molar ratio of S-enantiomer to R-enantiomer of the deuterated S-bupropion administered to the patient.

The therapeutic methods can be further characterized according to the magnitude of improvement in efficacy relative to administering an equimolar amount of non-isotopically enriched bupropion, e.g., non-isotopically enriched bupropion. In certain embodiments, the magnitude of improvement is at least a 10%, 20%, 30%, 40%, 50%, 60%, 70%, 80%, 90%, 100%, 125%, 150%, 175%, 200%, 250%, 300%, 350%, or 400% improvement. In certain embodiments, the magnitude of improvement is in the range of about 10% to 30%, about 30% to 50%, about 50% to 70%, about 70% to 90%, about 90% to 100%, about 100% to 125%, about 125% to 150%, about 150% to 175%, or about 175% to 200% improvement.

The therapeutic methods can be further characterized according to the magnitude of reduction in an adverse side effect (e.g., seizure) relative to administering an equimolar amount of non-isotopically enriched bupropion. In certain embodiments, the magnitude of reduction in an adverse side effect (e.g., seizure) is at least a 10%, 20%, 30%, 40%, 50%, 60%, 70%, 80%, 90%, 100%, 125%, 150%, 175%, 200%, 250%, 300%, 350%, or 400%. In certain embodiments, the magnitude of reduction in an adverse side effect is in the range of about 10% to 30%, about 30% to 50%, about 50% to 70%, about 70% to 90%, about 90% to 100% to 125%, about 125% to 150%, about 150% to 175%, or about 175% to 200%. In certain embodiments, the side effect is seizure, hepatic impairment, cardiovascular disorder (e.g., hypertension, hypotension, or palpitations), renal impairment, dizziness, constipation, anorexia, headache, dry mouth, agitation, or blurred vision. In certain embodiments, the side effect is seizure.

The therapeutic methods can be further characterized according to the magnitude of improvement in therapeutic index relative to administering an equimolar amount of non-isotopically enriched bupropion. In certain embodiments, the magnitude of improvement is at least a 1.1-, 1.5-, 2, 5-, 10-, 15-, 20-, 25-, 30-, 35-, 40-, 45-, 50-, 55-, 60-, 65-, or 70-fold improvement. In certain embodiments, the magnitude of improvement is at least a 30-, 35-, 40-, 45-, or 50-fold improvement. In certain embodiments, the magnitude of improvement is in the range of a 2-10-, 10-20-, 20-30-, 30-40-, 40-50-, or 50-60-fold improvement.

Manufacture of Medicaments

Another aspect of the disclosure provides for the use of a crystalline form of a deuterium-enriched compound described herein for the manufacture of a medicament. The medicament may be for treating one or more of the medical disorders described herein, such as treating depression, nicotine dependence, obesity, sexual dysfunction, neuropathic pain, or attention deficit hyperactivity disorder.

III. Dosing Considerations and Combination Therapy

Doses of a crystalline form of a compound provided herein vary depending on factors such as: specific indication to be treated; age and condition of a patient; and amount of second active agent used, if any. Generally, a compound provided herein may be used in an amount of from about 0.1 mg to about 1 g per day, or from about 0.1 mg to about 500 mg per day, and can be adjusted in a conventional fashion (e.g., the same amount administered each day of the treatment), in cycles (e.g., one week on, one week off), or in an amount that increases or decreases over the course of treatment. In other embodiments, the dose can be from about 1 mg to 1000 mg, from about 1 mg to about 450 mg, from about 0.1 mg to about 150 mg, from about 1 mg to about 300 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg. In yet other embodiments, the daily dose can be from about 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, 275 mg to 300 mg, 300 mg to 325 mg, 325 mg to 350 mg, 350 mg to 375 mg, 375 mg to 400 mg, 400 mg to 425 mg, or 425 mg to 450 mg. In certain embodiments, the deuterium-enriched bupropion is administered at a daily dosage in the range of about 125 mg to 150 mg, 150 mg to 175 mg, 175 mg to 200 mg, 200 mg to 225 mg, 225 mg to 250 mg, 250 mg to 275 mg, or 275 mg to 300 mg. In certain embodiments, the deuterium-enriched bupropion is administered at a daily dosage in the range of about 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, or 275 mg to 300 mg. In certain embodiments, the deuterium-enriched bupropion is administered at a daily dosage in the range of about 125 mg to 150 mg or 150 mg to 175 mg. In certain embodiments, the deuterium-enriched bupropion is administered at a daily dosage in the range of about 125 mg to 175 mg. In certain embodiments, the deuterium-enriched bupropion is administered at a daily dosage in the range of about 140 mg to 160 mg. In yet other embodiments, the deuterium-enriched bupropion is administered at a daily dosage in the range of about 50 mg to 175 mg, or about 125 mg to 175 mg. In yet other embodiments, the daily dose is less than about 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, or 450 mg. In yet other embodiments, the daily dose is less than about 125 mg, 150 mg, or 175 mg.

Combination Therapy

A crystalline form of the deuterium-enriched compound described herein, can be combined with other pharmacologically active compounds ("second active agents") in methods and compositions provided herein. Certain combinations may work synergistically in the treatment of particular types of diseases or disorders, and conditions and symptoms associated with such diseases or disorders. A crystalline form of the deuterium-enriched compound described herein, can also work to alleviate adverse effects associated with certain second active agents, and vice versa.

One or more second active ingredients or agents can be used in the methods and compositions provided herein. Second active agents can be large molecules (e.g., proteins) or small molecules (e.g., synthetic inorganic, organometallic, or organic molecules).

In certain embodiments, the combination therapy comprises a crystalline form of the deuterium-enriched compound described herein and one or more of naltrexone, liraglutide, topiramate, phentermine, semaglutide, and tirzepatide. Such combination therapy can be particular useful for the treatment of obesity or metabolic syndrome.

In certain embodiments, the combination therapy comprises a crystalline form of the deuterium-enriched compound described herein and zonisamide. In certain embodiments, the combination therapy comprises a crystalline form of the deuterium-enriched compound described herein and naltrexone (e.g., ultra-low dose naltrexone, very low dose naltrexone, low dose naltrexone). Such combination therapies can be particular useful for the treatment of obesity.

In certain other embodiments, the combination therapy comprises a crystalline form of the deuterium-enriched compound described herein and trazodone. Such combination therapy can be particular useful for the treatment of sexual dysfunction.

In certain other embodiments, the combination therapy comprises a crystalline form of the deuterium-enriched compound described herein and one or more serotonin and norepinephrine reuptake inhibitors (e.g., escitalopram, citalopram) or serotonin-norepinephrine reuptake inhibitors (e.g., venlafaxine, levomilnacipran). Such combination therapy can be particular useful for the treatment of depression and bipolar disorder.

In certain other embodiments, the combination therapy comprises a crystalline form of the deuterium-enriched compound described herein and a cytochrome P450 (CYP450) 2D6 substrate (e.g., dextromethorphan, tetrabenazine). Such combination therapy can be particularly useful for a range of disorders including depression, Alzheimer's disease agitation, smoking cessation, Huntington's chorea, and tardive dyskinesia.

Administration of a crystalline form of the deuterium-enriched compound described herein and the second active agent to a patient can occur simultaneously or sequentially by the same or different routes of administration. The suitability of a particular route of administration employed for a particular second active agent will depend on the second active agent itself (e.g., whether it can be administered orally without decomposing prior to entering the blood stream) and the disease being treated. One route of administration for compounds provided herein is oral. Routes of administration for the second active agents or ingredients are known to those of ordinary skill in the art. See, e.g., Physicians' Desk Reference (60$^{th}$ Ed., 2006).

IV. Pharmaceutical Compositions

The disclosure provides pharmaceutical compositions comprising a crystalline form of the deuterium-enriched compound described herein, such as a crystalline form of a compound of Formula (I), and a pharmaceutically acceptable carrier. In certain embodiments, the pharmaceutical compositions comprise a therapeutically effective amount of a crystalline form of the deuterium-enriched compound described herein, such as a crystalline form of a compound of Formula (I), formulated together with one or more pharmaceutically acceptable carriers (additives) and/or diluents. As described in detail below, the pharmaceutical compositions of the present disclosure may be specially formulated for administration in solid or liquid form, including those adapted for the following: (1) oral administration, for example, drenches (aqueous or non-aqueous solutions or suspensions), tablets (e.g., those targeted for buccal, sublingual, and/or systemic absorption), boluses, powders, granules, pastes for application to the tongue; (2) parenteral administration by, for example, subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

Pharmaceutical compositions can be used in the preparation of individual, single unit dosage forms. Pharmaceutical compositions and dosage forms provided herein comprise a crystalline form of a deuterium-enriched compound described herein. Pharmaceutical compositions and dosage forms can further comprise one or more excipients. Additionally, pharmaceutical compositions and dosage forms provided herein can comprise one or more additional active ingredients. Examples of optional second, or additional, active ingredients are described above.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another and will be readily apparent to those skilled in the art. See, e.g., Remington's Pharmaceutical Sciences, 18th ed., Mack Publishing, Easton PA (1990).

The suitability of a particular excipient may depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose or other mono- or disaccharides. As used herein, the term "lactose-free" means that the amount of lactose present, if any, is insufficient to substantially increase the degradation rate of an active ingredient. Lactose-free compositions can comprise excipients that are well known in the art and are listed, for example, in the U.S. Pharmacopeia (USP) 25-NF20 (2002). In general, lactose-free compositions comprise active ingredients, a binder/filler, and a lubricant in pharmaceutically compatible and pharmaceutically acceptable amounts. In another aspect, lactose-free dosage forms comprise active ingredients, microcrystalline cellulose, pre-gelatinized starch, and magnesium stearate.

Also provided are anhydrous pharmaceutical compositions and dosage forms comprising active ingredients. Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected. An anhydrous pharmaceutical composition should be prepared and stored such that its anhydrous nature is maintained. Accordingly, anhydrous compositions are, in another aspect, packaged using materials known to prevent exposure to water such that they can be included in suitable formulary kits. Examples of suitable packaging include, but are not limited to, hermetically sealed foils, plastics, dose containers (e.g., vials), blister packs, and strip packs.

Also provided are pharmaceutical compositions and dosage forms that comprise one or more compounds that reduce the rate at which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients.

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton PA (1990).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In another aspect, the disclosure provides oral dosage forms that are tablets or capsules, in which case solid excipients are employed. In another aspect, the tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose, methyl cellulose, hydroxypropyl methyl cellulose, microcrystalline cellulose), polyvinyl-pyrrolidone, pre-gelatinized starch, and mixtures thereof.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in another aspect, present in from about 50 to about 99 weight percent of the pharmaceutical composition or dosage form.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In another aspect, pharmaceutical compositions comprise from about 0.5 to about 15 weight percent of disintegrant, or from about 1 to about 5 weight percent of disintegrant. Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laurate, agar, and mixtures thereof. Additional lubricants include, for example, a Syloid® silica gel (AEROSIL200, manufactured by W. R. Grace Co. of Baltimore, MD), a coagulated aerosol of synthetic silica (marketed by Degussa Co. of Piano, TX), CAB-O-SIL (a pyrogenic silicon dioxide product sold by Cabot Co. of Boston, MA), and mixtures thereof. If used at all, lubricants may be used in an amount of less than about 1 weight percent of the pharmaceutical compositions or dosage forms into which they are incorporated.

In another aspect, the disclosure provides a solid oral dosage form comprising a compound provided herein, anhydrous lactose, microcrystalline cellulose, polyvinylpyrrolidone, stearic acid, colloidal anhydrous silica, and gelatin.

Active ingredients provided herein can also be administered by controlled release means or by delivery devices that are well known to those of ordinary skill in the art. Such dosage forms can be used to provide slow or controlled release of one or more active ingredients using, for example, hydroxypropyl methyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active agents provided herein. In another aspect, the disclosure provides single unit dosage forms suitable for oral administration such as, but not limited to, tablets, capsules, gel caps, and caplets that are adapted for controlled release.

Parenteral dosage forms can be administered to patients by various routes including, but not limited to, subcutaneous, intravenous (including bolus injection), intramuscular, and intraarterial. Administration of a parenteral dosage form bypasses a patient's natural defenses against contaminants, and thus, in these aspects, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of a compound provided herein.

Topical and mucosal dosage forms provided herein include, but are not limited to, sprays, aerosols, solutions, emulsions, suspensions, eye drops or other ophthalmic preparations, or other forms known to one of skill in the art. See, e.g., Remington's Pharmaceutical Sciences, 16th and 18th eds., Mack Publishing, Easton PA (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein are well known to those skilled in the pharmaceutical arts and depend on the particular tissue to which a given pharmaceutical composition or dosage form will be applied. In another aspect, excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions, or gels, which are nontoxic and pharmaceutically acceptable. Moisturizers or humectants can also be added to pharmaceutical compositions and dosage forms. Examples of additional ingredients are well known in the art. See, e.g., Remington's Pharmaceutical Sciences, 16th and 18th eds., Mack Publishing, Easton PA (1980 & 1990).

The pH of a pharmaceutical composition or dosage form may also be adjusted to improve delivery of one or more active ingredients. Also, the polarity of a solvent carrier, its ionic strength, or tonicity can be adjusted to improve delivery. Compounds such as stearates can also be added to pharmaceutical compositions or dosage forms to alter the hydrophilicity or lipophilicity of one or more active ingredients so as to improve delivery. In other aspects, stearates can serve as a lipid vehicle for the formulation, as an emulsifying agent or surfactant, or as a delivery-enhancing or penetration-enhancing agent.

In another aspect, the active ingredients provided herein are not administered to a patient at the same time or by the same route of administration. In another aspect, provided are kits which can simplify the administration of appropriate amounts of active ingredients.

In another aspect, the disclosure provides a kit comprising a dosage form of a compound provided herein. Kits can further comprise additional active ingredients or a pharmacologically active mutant or derivative thereof, or a combination thereof. Examples of the additional active ingredients include, but are not limited to, those disclosed herein.

In other aspects, the kits can further comprise devices that are used to administer the active ingredients. Examples of such devices include, but are not limited to, syringes, drip bags, patches, and inhalers.

V. Definitions

To facilitate an understanding of the present disclosure, a number of terms and phrases are defined below.

The term "compound" refers to a quantity of molecules that is sufficient to be weighed, tested for its structural identity, and to have a demonstrable use (e.g., a quantity that can be shown to be active in an assay, an in vitro test, or in vivo test, or a quantity that can be administered to a patient and provide a therapeutic benefit).

Unless indicated otherwise, when a D is specifically recited at a position or is shown in a formula, this D represents a mixture of hydrogen and deuterium where the amount of deuterium is about 100% (i.e., the abundance of deuterium ranges from greater than 90% up to 100%). In certain embodiments, the abundance of deuterium in D is from 95% to 100%, or from 97% to 100%.

The term "patient" refers to organisms to be treated by the methods of the present disclosure. Such organisms preferably include, but are not limited to, mammals (e.g., murines, simians, equines, bovines, porcines, canines, felines, and the like), and most preferably includes humans.

As used herein, the term "effective amount" refers to the amount of a compound sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating, or eliminating, that results in the improvement of the condition, disease, disorder, and the like, or ameliorating a symptom thereof.

"Therapeutically effective amount" includes an amount of a compound of the disclosure that is effective when administered alone or in combination to treat the desired condition or disorder. "Therapeutically effective amount" includes an amount of the combination of compounds claimed that is effective to treat the desired condition or disorder. The combination of compounds can be additive and is preferably a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as single agents. In general, a synergistic effect is most clearly demonstrated at sub-optimal concentrations of the compounds. Synergy can be in terms of lower incidence of adverse side effects and/or toxicity, increased efficacy, or some other beneficial effect of the combination compared with the individual components.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable excipient" refers to any of the standard pharmaceutical excipients, such as a phosphate-buffered saline solution, water, emulsions (e.g., such as oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA [1975].

Throughout the description, where compositions are described as having, including, or comprising specific components, or where processes and methods are described as having, including, or comprising specific steps, it is contemplated that, additionally, there are compositions of the present disclosure that consist essentially of, or consist of, the recited components, and that there are processes and methods according to the present disclosure that consist essentially of, or consist of, the recited processing steps.

As a general matter, if a variable is not accompanied by a definition, then the previous definition of the variable controls.

Finally, the disclosure may be embodied in other specific forms without departing from the spirit or essential attributes thereof. This disclosure encompasses all combinations of aspects and embodiments of the disclosure noted herein. It is understood that any and all aspects of the disclosure may be taken in conjunction with any other aspects and/or embodiments to describe additional aspects. It is also to be understood that each individual element of the aspects is intended to be taken individually as its own independent aspect. Furthermore, any element of an aspect is meant to be combined with any and all other elements from any aspect to describe an additional aspect.

EXAMPLES

The disclosure, now being generally described, will be more readily understood by reference to the following examples, which are included merely for purposes of illustration of certain aspects and embodiments of the present disclosure, and are not intended to limit the disclosure.

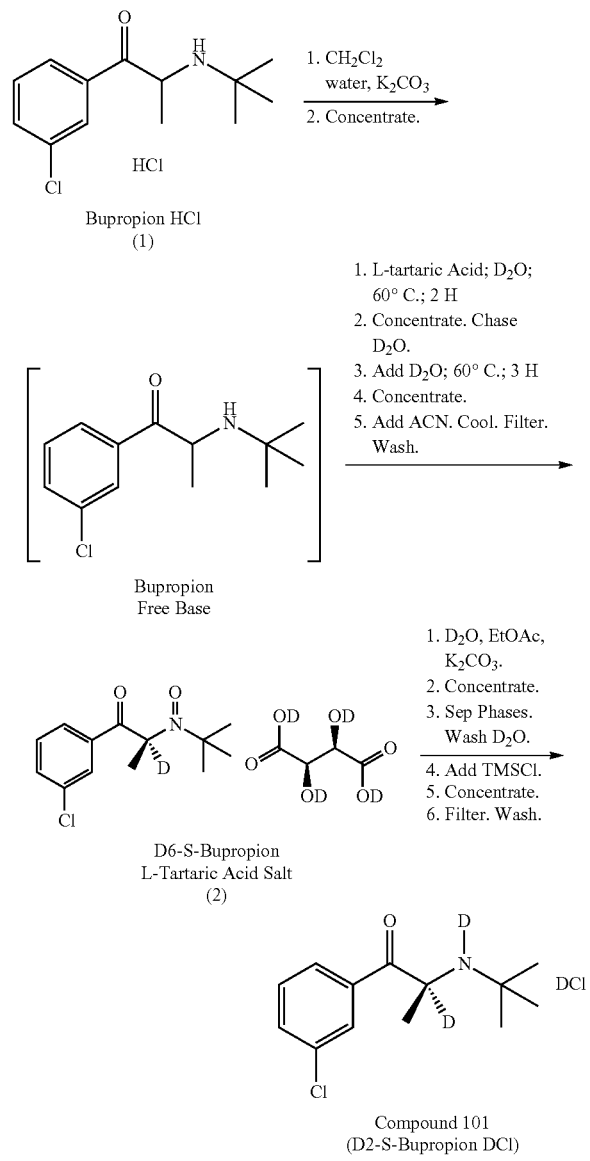

Compound (2): Compound (2) was produced starting with 2.54 kg of Compound (1). Compound (1) was dissolved in a mixture of dichloromethane (DCM, 3.7 L) and water (5.1 L). The pH of the biphasic mixture was adjusted to about pH 9.8 by the addition of 47% aqueous $K_2CO_3$ (3.17 kg). The phases were separated. The aqueous layer was back extracted with DCM (0.96 L) and the organic phases were combined. The solution of bupropion free base in DCM was concentrated to about 2.4 L. A solution of L-tartaric acid (1.26 kg) in $D_2O$ (5.1 kg) was added to the bupropion free base solution and an additional 0.9 kg $D_2O$ was added as a rinse. The mixture was concentrated to remove residual DCM, then it was heated to about 55° C. for about 4 hours. The mixture was then concentrated by vacuum distillation until the volume reached about 4.3 L. Another charge of $D_2O$ (5.8 kg) was added and the mixture was distilled again to about 4.3 L. A third charge of $D_2O$ (6.9 kg) was added and the mixture was heated at about 55° C. for about 4 hours. The mixture was concentrated by vacuum distillation to about 4.3 L. The mixture was cooled to about 10° C. then diluted with acetonitrile (ACN, 7.2 L including rinse) to transfer to a reactor before being further diluted with ACN (31.8 L). The mixture was seeded with Compound (2) (1.43 g, obtained from a smaller batch made using the process described herein but which did not utilize seeding) to give a slurry and the mixture was cooled to about −25 to about −28° C. for 12 hours. The mixture was filtered, and the solid cake was rinsed with cold ACN (6.4 L, 10° C.). The solid was then dried by a stream of nitrogen for about 3 days. This first batch afforded 1.461 kg of Compound (2) with an estimated purity of 94.4% (by quantitative HPLC), and a 37.8% yield. Using the same process starting with 2.71 kg of Compound (1), a second batch of 1.623 kg of Compound (2) was obtained with 94.3% purity (by quantitative HPLC), and a 39.3% yield.

Compound 101: Compound (2) (3.08 kg) was dissolved in a mixture of ethyl acetate (15.6 L) and $D_2O$ (6.03 kg) and the pH was adjusted to about 9.6 by slow addition of a solution of $K_2CO_3$ in $D_2O$ (1.9 kg $K_2CO_3$ in 2.3 kg $D_2O$) followed by additional solid $K_2CO_3$ (525 g). The biphasic mixture was distilled under vacuum to remove tert-butylamine (as Compound (2) contained about 5% of tert-butylamine L-tartaric acid salt as an impurity) until reaching a final volume of 24.5 L. Ethyl acetate (8.6 L) was added and the mixture was stirred. After settling for 5 minutes, the phases were separated, and the organic layer was washed with $D_2O$ (about 2.9 kg) to remove residual potassium salts. The first $D_2O$ layer was back extracted with ethyl acetate (10.2 L), then the back extraction was washed with the $D_2O$ used to wash the first ethyl acetate layer.

The ethyl acetate layers were combined then charged into a reactor by vacuum transfer through a 1 micron Whatman cartridge filter to remove particulates. The mixture was cooled to about 15° C. and chlorotrimethylsilane (TMSCl, 948 g clarified by filtration through a sintered glass frit to give 904 g of clarified TMSCl) was added slowly over about 20 minutes to generate the DCl salt. After TMSCl addition, the mixture was seeded with Compound 101 (3.2 g, obtained from another batch at about 500 g scale of the DCl salt, made using the process described herein but which did not utilize seeding). The slurry was held at 15 to 22° C. overnight. The mixture went through a series of distillations, each followed by addition of fresh ethyl acetate, to remove $D_2O$, ethanol, and acetic acid (i.e., from 40 L to 17 L; then, after addition of 13.3 L ethyl acetate, from 30.3 L to 13.3 L; then, after addition of 6 L ethyl acetate, from 19.3 L to 13 L; after another after addition of 6 L ethyl acetate, from 19 L to 13.3 L). After the distillations were complete, 17 L ethyl acetate were added under atmospheric pressure nitrogen, and the mixture was stirred overnight. The solid was collected by vacuum filtration then displacement-washed with ethyl acetate (8.3 L). The solid was dried in a room temperature nitrogen stream over about 3 days. The reaction afforded 1.798 kg, a 94.8% yield.

$^1$H NMR spectrum of Compound 101 is shown in FIG. 1.

Chemical purity by HPLC (Agilent 1100 HPLC. Zorbax XDB-C18 50×4.6 mm 3.5 micron column; Solvent A: Water (0.1% trifluoroacetic acid, TFA); Solvent B: Acetonitrile (0.07% TFA); Gradient: 95% A to 95% B over 5 min; hold for 1 min; recycle over 1 min; 30 s hold; Flow Rate: 1.5 mL/min; UV Detection: 210 nm; Column temperature: 30° C.): 100%.

Chiral purity by HPLC (Agilent 1100 HPLC. Chiralcel OD-H 250×4.5 mm 5.0 micron column; Solvent A: Hexane; Solvent B: Isopropanol, TFA, isopropylamine (1000:10:5 v/v/v); Isocratic—90% A, 10% B for 10 min; Flow Rate: 1.5 mL/min; UV Detection: 254 nm; Column temperature: 23° C.): 99.88% ee.

Water Content (Karl-Fischer): 577 ppm

% protonated $^1$H (DMSO-d6): 0.77%; (MS (ESI+) for $C_{13}H_{17}DCINO$ m/z 241.0 (M+H)$^+$; no peak at m/z 240 (protonated) and intensity of peak at m/z 244 consistent with absence of tetradeutero (expected intensity due to natural abundance isotopes). It should be noted that N-D exchanges to N—H during analysis (HPLC method uses water as solvent).

Elemental analysis: Anal. Calcd for $C_{13}H_{16}D_3Cl_2NO$: C, 55.92; H, 6.86; N, 5.02; Cl, 25.39. Found: C, 55.91; H, 6.86; N, 5.00; Cl, 25.46.

Example 2. Xray Powder Diffraction (XRPD) Analyses

XRPD analyses were run on a Bruker D8 Advance diffractometer having a goniometer radius of 280 mm and working in Bragg-Brentano geometry. The radiation used was Ni-filtered CuKα; the detector used was a silicon strip (LynxEye) detector. The range analyzed was 3-40' in 2θ with a step of 0.02°. The sample holder used was a zero-background silicon monocrystal. The data obtained were analyzed with Diffrac.Eva software version 4.3.

Figure 2:
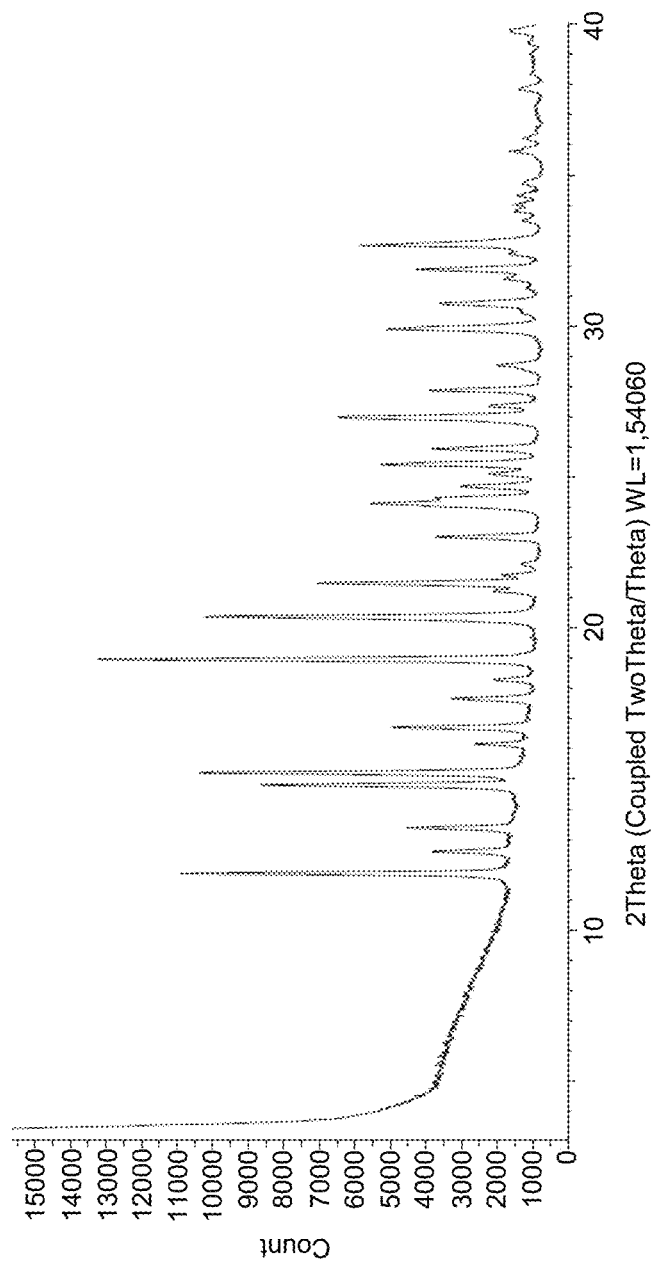
FIG. 2 is an exemplary X-ray powder diffraction (XRPD) pattern of bupropion HCl.

The XRPD diffractogram for Bupropion HCl is shown in FIG. 2. The peak listing for the Bupropion HCl XRPD is in Table 1. The positions of the peaks correspond to XRPD data reported in the literature for form 1 of Bupropion HCl.

TABLE 1

XRPD peak listing for Bupropion HCl

| Index | Angle [° in 2θ] | d-spacings [Å] | Rel. intensity |
|---|---|---|---|
| 1 | 6.40 | 13.8 | 0.9% |
| 2 | 12.00 | 7.37 | 8.0% |
| 3 | 12.71 | 6.96 | 11.1% |
| 4 | 13.51 | 6.55 | 0.9% |
| 5 | 14.92 | 5.93 | 3.0% |
| 6 | 15.33 | 5.77 | 2.6% |
| 7 | 16.27 | 5.44 | 1.4% |
| 8 | 16.83 | 5.26 | 1.6% |
| 9 | 17.77 | 4.99 | 0.8% |
| 10 | 19.06 | 4.65 | 100.0% |
| 11 | 20.49 | 4.33 | 2.7% |
| 12 | 21.34 | 4.16 | 0.8% |
| 13 | 21.61 | 4.11 | 4.5% |
| 14 | 23.13 | 3.84 | 0.9% |
| 15 | 24.25 | 3.67 | 2.9% |

TABLE 1-continued

XRPD peak listing for Bupropion HCl

| Index | Angle [° in 2θ] | d-spacings [Å] | Rel. intensity |
|---|---|---|---|
| 16 | 25.48 | 3.49 | 6.2% |
| 17 | 26.05 | 3.42 | 1.1% |
| 18 | 27.05 | 3.29 | 3.1% |
| 19 | 27.47 | 3.24 | 3.2% |
| 20 | 28.00 | 3.18 | 2.1% |

The XRPD diffractogram for Compound 101 is shown in FIG. 3. The peak listing for Compound 101 XRPD is in Table 2.

TABLE 2

XRPD peak listing for Compound 101

| Index | Angle [° in 2θ] | d-spacings [Å] | Rel. intensity |
|---|---|---|---|
| 1 | 6.78 | 13.0 | 1.5% |
| 2 | 8.71 | 10.2 | 9.6% |
| 3 | 11.85 | 7.46 | 7.8% |
| 4 | 12.26 | 7.22 | 100.0% |
| 5 | 13.00 | 6.80 | 7.1% |
| 6 | 13.43 | 6.59 | 18.5% |
| 7 | 14.11 | 6.27 | 12.9% |
| 8 | 14.29 | 6.19 | 5.8% |
| 9 | 15.29 | 5.79 | 54.7% |
| 10 | 15.78 | 5.61 | 42.5% |
| 11 | 16.85 | 5.26 | 21.2% |
| 12 | 17.32 | 5.12 | 12.7% |
| 13 | 17.56 | 5.05 | 4.1% |
| 14 | 18.01 | 4.92 | 7.7% |
| 15 | 18.40 | 4.82 | 26.7% |
| 16 | 18.83 | 4.71 | 22.9% |
| 17 | 20.24 | 4.38 | 1.7% |
| 18 | 21.99 | 4.04 | 20.7% |
| 19 | 22.80 | 3.90 | 20.1% |
| 20 | 23.47 | 3.79 | 8.6% |

As shown by a comparison of FIGS. 2 and 3, Compound 101 crystalline form has an XRPD diffractogram distinctly different from than that of bupropion HCl.

Example 3. Differential Scanning Calorimetry (DSC) Analyses

DSC analyses were run on a Mettler-Toledo DSC-3 cell. Accurately weighed 2-4 mg samples were placed in aluminum pans with pierced lids and heated at 10° C./min from 30° C. to 300° C. under nitrogen flow. The data obtained were analyzed with Star$^e$ software version 16.00.

Figure 4:
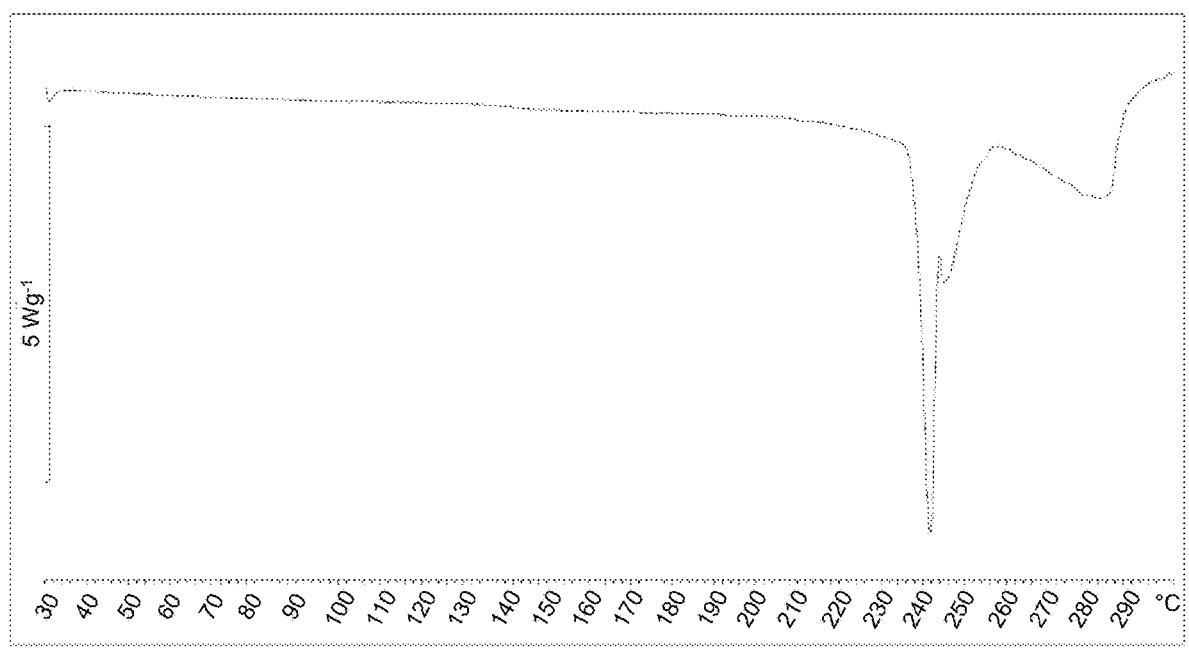
FIG. 4 is an exemplary differential scanning calorimetry (DSC) pattern of bupropion HCl.

The DSC of Bupropion HCl (shown in FIG. 4) matches the DSC data reported in the scientific literature for form 1 of Bupropion HCl, thus confirming the identity of the crystalline form. The complex endothermic event at 238° C. is a melting immediately followed by decomposition.

The DSC of Compound 101 (shown in FIG. 5) shows a complex event, with a small exothermic event preceding a complex endotherm (melting with decomposition) in the range 225-235° C.

Example 4. Particle Size Distribution and Microscopy

Particle size distribution was analyzed using laser diffraction. The apparatus used was a Malvern Mastersizer 3000 equipped with a Hydro 3000S cell for wet dispersion measurements. The measuring range was 0.01-3500 μm, the dispersant used was Isopar G (dispersant RI 1.42). The scattering model used was Mie (material RI 1.50, AI 0.10). The cell was cleaned, filled with dispersant, aligned and the background measured (30 sec. for red light, 10 seconds for blue light). The pump speed was set at 2800 rpm. About 100 mg of the sample were dispersed in 0.5 ml of 2% w/w soy lecithin solution in isopar G, stirred gently with a glass rod and brought to 10 ml with isopar G. The suspension was sonicated for about a minute, then added dropwise to the measurement cell until an obscuration of 10-20% was obtained. The sample was then measured for 20 seconds with red light and 10 seconds with blue light. The results given, expressed in Dv(10), Dv(50) and Dv(90) are the average of three consecutive measurements (Table 3).

Results

TABLE 3

| Particle size distribution | | |
|---|---|---|
| | Bupropion HCl | Compound 101 |
| Dv(10) | 4.9 μm | 7.1 μm |
| Dv(50) | 64 μm | 31 μm |
| Dv(90) | 208 μm | 179 μm |

Light Microscopy

In order to better interpret the laser diffraction results and to verify correct dispersion of the sample, a drop of the suspension used for the analysis was placed on a microscope glass slide, covered with a glass coverslip and observed with a Zeiss Axiostar microscope at 100× magnification in direct unfiltered light. The images obtained are reported in FIG. 6 (Bupropion HCl) and FIG. 7 (Compound 101). In both cases, the dispersion was found adequate. Crystals of Compound 101 were found to be needle-shaped (FIG. 7).

INCORPORATION BY REFERENCE

All references listed herein are individually incorporated in their entirety by reference.

EQUIVALENTS

Numerous modifications and variations of the disclosure are possible in light of the above teachings. It is therefore to be understood that within the scope of the appended claims, the disclosure may be practiced otherwise that as specifically described herein.

The invention claimed is:

1. A crystalline form of a compound represented by Formula (I):

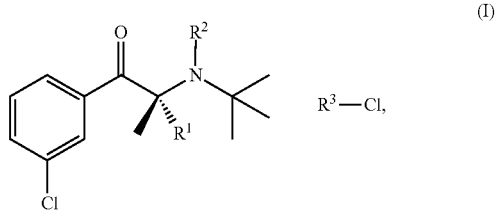

wherein $R^1$, $R^2$, and $R^3$ are each independently H or D, provided that the abundance of deuterium in each of $R^1$, $R^2$, and $R^3$ is at least 30%, and wherein the crystalline form of the compound is characterized by an X-ray powder diffraction pattern comprising peaks at the following diffraction angles (2θ): 12.3°±0.2°, 15.3°±0.2°, and 15.8°±0.2°.

2. The crystalline form of claim 1, wherein the crystalline form of the compound is characterized by an X-ray powder diffraction pattern further comprising one or more peaks at the following diffraction angles (2θ): 13.4°±0.2°, 14.1°±0.2°, 16.9°±0.2°, 17.3°±0.2°, 18.4°±0.2°, 18.8°±0.2°, 22.0°±0.2°, and 22.8°±0.2°.

3. The crystalline form of claim 1, wherein the crystalline form of the compound has a melting point onset as determined by differential scanning calorimetry at about 225° C. to about 235° C.

4. The crystalline form of claim 1, wherein the crystalline form of the compound is anhydrous.

5. The crystalline form of claim 1, wherein the abundance of deuterium in $R^1$ is at least 50%.

6. The crystalline form of claim 1, wherein the abundance of deuterium in $R^2$ is at least 50%.

7. The crystalline form of claim 1, wherein the abundance of deuterium in $R^3$ is at least 50%.

8. The crystalline form of claim 1, wherein the abundance of deuterium in each of $R^1$, $R^2$, and $R^3$ is at least 50%.

9. The crystalline form of claim 1, wherein the abundance of deuterium in each of $R^1$, $R^2$, and $R^3$ is at least 75%.

10. The crystalline form of claim 1, wherein the abundance of deuterium in each of $R^1$, $R^2$, and $R^3$ is at least 90%.

11. The crystalline form of claim 1, wherein the abundance of deuterium in each of $R^1$, $R^2$, and $R^3$ is at least 95%.

12. The crystalline form of claim 1, wherein the crystalline form of the compound is characterized by a stereochemical purity of at least 75% enantiomeric excess at the carbon bearing variable $R^1$.

13. The crystalline form of claim 1, wherein the crystalline form of the compound is characterized by a stereochemical purity of at least 90% enantiomeric excess at the carbon bearing variable $R^1$.

14. The crystalline form of claim 1, wherein the crystalline form of the compound is characterized by a stereochemical purity of at least 95% enantiomeric excess at the carbon bearing variable $R^1$.

15. A pharmaceutical composition comprising a crystalline form of claim 1, and a pharmaceutically acceptable excipient.

* * * * *